United States Patent [19]

Clemence et al.

[11] Patent Number: 5,674,864
[45] Date of Patent: Oct. 7, 1997

[54] N-SUBSTITUTED DERIVATIVES OF α-MERCAPTO ALKYLAMINES, THEIR PREPARATION PROCESS AND THE INTERMEDIATES OBTAINED, THEIR USE AS MEDICAMENTS AND THE COMPOSITIONS CONTAINING THEM

[75] Inventors: François Clemence; Odile Le Martret, both of Paris; Francis Petit, Bondy, all of France

[73] Assignee: Roussel Uclaf, France

[21] Appl. No.: 449,290

[22] Filed: May 24, 1995

Related U.S. Application Data

[62] Division of Ser. No. 970,117, Nov. 2, 1992, which is a division of Ser. No. 725,985, Jul. 5, 1991, Pat. No. 5,190,974.

[30] Foreign Application Priority Data

Jul. 5, 1990 [FR] France ..................... 90 08539

[51] Int. Cl.$^6$ .................. A61K 31/54; A61K 31/535; C07D 401/02; C07D 403/02
[52] U.S. Cl. .................. 514/212; 514/227.5; 514/237.5; 514/255; 514/330; 514/423; 540/575; 540/608; 544/58.4; 544/58.1; 544/168; 544/359; 544/386; 546/226; 548/567; 548/568
[58] Field of Search .................. 544/58.4, 58.1, 544/168, 359, 386; 546/226; 548/567, 568; 514/212, 227.5, 237.5, 255, 330, 423; 540/575, 608

[56] References Cited

U.S. PATENT DOCUMENTS 5,041,552   8/1991   Hodges et al. .................. 548/263.8

*Primary Examiner*—Matthew V. Grumbling
*Attorney, Agent, or Firm*—Bierman, Muserlian and Lucas LLP

[57] ABSTRACT

Novel α-mercapto-alkylamines in all possible racemic, enantiomeric and diastereoisomeric forms of the formula

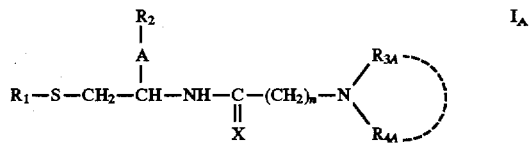

wherein the substituents are as defined in the specification.

9 Claims, No Drawings

N-SUBSTITUTED DERIVATIVES OF α-MERCAPTO ALKYLAMINES, THEIR PREPARATION PROCESS AND THE INTERMEDIATES OBTAINED, THEIR USE AS MEDICAMENTS AND THE COMPOSITIONS CONTAINING THEM

PRIOR APPLICATIONS

This application is a division of U.S. patent application Ser. No. 970,117 filed Nov. 2, 1992 which is a division of U.S. patent application Ser. No. 725,985 filed Jul. 5, 1991, now U.S. Pat. No. 5,190,974.

STATE OF THE ART

Related prior art includes U.S. Pat. No. 4,071,685 and U.S. Pat. No. 4,724,235 and Biochemical and Biophysical Research Communications, Vol. 143, No. 1, pp 44 to 51 (Feb. 27, 1987).

OBJECTS OF THE INVENTION

It is an object of the invention to provide the novel compounds of formula $I_A$ and their non-toxic, pharmaceutically acceptable acid addition salts and a process and novel intermediates for their preparation.

It is another object of the invention to provide novel analgesic compositions and a novel method of relieving pain in warm-blooded animals.

These and other objects and advantages of the invention will become obvious from the following detailed description.

THE INVENTION

The novel compounds of the invention are selected from the group consisting of α-mercapto-alkylamines in all possible racemic, enantiomeric and diastereoisomeric forms of the formula

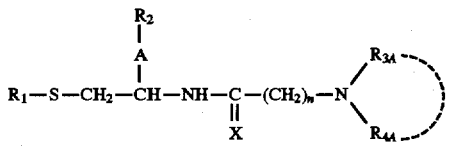

wherein n is an integer from 0 to 4, $R_1$ is hydrogen or

or $R_5$ is selected from the group consisting of optionally substituted alkyl of 1 to 6 carbon atoms, optionally substituted alkenyl and alkynyl of 2 to 6 carbon atoms, optionally substituted and optionally unsaturated monocyclic ring of 5 to 7 links and condensed rings of 8 to 10 links and optionally containing at least one heteroatom selected from the group consisting of —O—, —S— and nitrogen and

$R_{10}$ and $R_{11}$ together with the nitrogen atom to which they are attached form a monocyclic ring of 5 to 7 links or condensed rings of 8 to 10 links optionally substituted and optionally containing at least one heteroatom selected from the group consisting of —O—, —S— and nitrogen or $R_{10}$ and $R_{11}$ are individually selected from the group consisting of hydrogen, optionally substituted alkyl of 1 to 6 carbon atoms, optionally substituted alkenyl and alkynyl of 2 to 6 carbon atoms and optionally substituted monocyclic aryl of 5 to 7 links or condensed aryl of 8 to 10 links optionally containing at least one heteroatom selected from the group consisting of —O—, —S— and nitrogen, A is selected from the group consisting of alkylene of 1 to 6 carbon atoms and alkenylene of 2 to 6 carbon atoms, both optionally substituted with —OH or alkoxy of 1 to 6 carbon atoms and a single bond, $R_2$ is optionally substituted monocyclic ring of 5 to 7 links or condensed rings of 8 to 10 links optionally interrupted with at least one heteroatom selected from the group consisting of —O—, —S— and nitrogen, X is oxygen or sulfur, $R_{3A}$ and $R_{4A}$ together with the nitrogen to which they are attached form an optionally substituted monocyclic ring of 5 to 7 links or condensed rings of 8 to 10 links optionally containing at least one heteroatom selected from the group consisting of —O—, —S— and nitrogen or are individually selected from the group consisting of hydrogen, —OH, alkoxy of 1 to 6 carbon atoms, acyl and acyloxy of up to 6 carbon atoms, salified or esterified carboxy, —CN, optionally substituted alkyl of 1 to 6 carbon atoms, optionally substituted alkenyl and alkynyl of 2 to 6 carbon atoms, $R_c$—, $R_c$—O—, $R_c$ is selected from the group consisting of optionally substituted aliphatic or aryl monocyclic ring of 5 to 7 links or condensed rings of 8 to 10 links optionally containing at least one heteroatom selected from the group consisting of —O—, —S— and nitrogen,

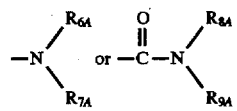

$R_{6A}$, $R_{7A}$, $R_{8A}$ and $R_{9A}$ are individually selected from the group consisting of hydrogen, —OH, alkyl, alkoxy, acyl and acyloxy of up to 6 carbon atoms, free, salified or esterified carboxy, phenoxy, phenyl, benzyl, phenethyl, azepine, piperidyl, morpholino, pyrrolidinyl and piperazinyl optionally substituted on the second nitrogen by —OH or alkyl, alkoxy or phenyl, the latter three being optionally substituted with at least one member of the group consisting of halogen, —CF₃, hydroxyl, CH₃O—, ethoxy, —CH₃ and ethyl or $R_{6A}$ and $R_{7A}$ and $R_{8A}$ and $R_{9A}$ together with the nitrogen atom to which they attached form a member of the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl, thiomorpholinyl, azepinyl and indolyl, all optionally substituted with at least one member of the group consisting of halogen, —OH, —CF₃ and alkyl and alkoxy of 1 to 6 carbon atoms and their non-toxic, pharmaceutically acceptable acid addition salts.

Among the preferred compounds of the invention are those of the formula

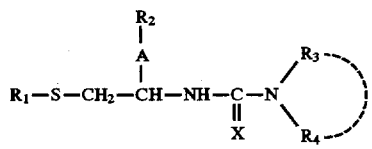

wherein $R_1$, $R_2$, A and X have the above definitions and $R_3$ and $R_4$ have the definitions of $R_{3A}$ and $R_{4A}$ other than $R_c$— and $R_cO—$ and their non-toxic, pharmaceutically acceptable acid addition salts.

Examples of alkyl are preferably methyl, ethyl, propyl, isopropyl, butyl, isobutyl, sec-butyl and tert-butyl but can also be pentyl or hexyl and particularly isopentyl and isohexyl. Examples of alkenyl are preferably vinyl, allyl, 1-propenyl, butenyl and particularly 1-butenyl or pentenyl. Examples of alkynyl are preferably ethynyl, propargyl, butynyl or pentynyl.

The monocyclic ring and condensed rings are saturated or unsaturated carbocyclic or heterocyclic, it being understood that the heterocyclics can contain one or more heteroatoms selected from oxygen, nitrogen or sulfur and that when these heterocyclics contain more than one heteroatom, the heteroatoms of these heterocyclic can be identical or different.

The monocyclic ring preferably contains 5 to 7 links and among the saturated carbocyclic monocyclic rings, are cyclohexyl and cyclopentyl. Among the unsaturated carbocyclic monocyclic rings are cyclopentenyl, cyclohexenyl, cyclopentadienyl, cyclohexadienyl and carbocyclic aryl such as phenyl.

Among the saturated heterocyclic monocyclic rings are pyrrolidinyl, imidazolidinyl, pyrazolidinyl, piperidyl, piperazinyl, morpholinyl, thiomorpholinyl and azepinyl. Among the unsaturated heterocyclic monocyclic rings are thienyl, furyl, pyrannyl, pyrrolyl, imidazolyl, pyrazolyl, pyridyl, pyrazinyl, pyrimidinyl, pyridazinyl, thiazolyl, oxazolyl, furazannyl, pyrrolinyl such as delta-2-pyrrolinyl, imidazolinyl such as delta-2-imidazolinyl, pyrazolinyl such as delta-3-pyrazolinyl, as well as the position isomers of the heteroatom or heteroatoms that can be contained by these such as isothiazolyl or isoxazolyl.

The condensed rings preferably contain 8 to 10 links. Among the saturated carbocyclic condensed rings are bicyclo[4,4,0]decyl and bicyclo[4,4,1]undecyl. Among the unsaturated carbocycic condensed rings are aryl such as naphthyl, indenyl and phenanthryl. Among the saturated heterocyclic condensed rings are 1-oxa-1-spiro [4,5]decane, tetrahydropyran-2-spirocyclohexane, cyclohexanespiro -2-(tetrahydrofuran) and 1,10-diaza-anthr-4-yl.

Among the unsaturated heterocyclic condensed rings are benzothienyl, naphtho[2,3-b]thienyl, indanyl, indenyl, thianthrenyl, isobenzofurannyl, chromenyl, xanthenyl, phenoxathiinyl, indolizinyl, isoindolyl, 3H- indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, beta-carbolinyl, acridinyl, phenazinyl, phenothiazinyl, phenoxazinyl, indolinyl, isoindolinyl as well as condensed polycyclic systems constituted by heterocyclic monocyclics as defined such as furo[2,3-b] pyrrole or thieno[2,3-b]furan.

Alkylene preferably is methylene, ethylene, propylene, trimethylene, tetramethylene, pentamethylene, hexamethylene, hydroxymethylene, hydroxypropylene, methoxypropylene or 2-methoxy tetramethylene. Alkenylene preferably is vinylene, propenylene or butenylene such as 2-butylene, hydroxyethenylene or 1-methoxy-2-butenylene. The alkoxy is preferably methoxy or ethoxy, but can also be propoxy, isopropoxy or butoxy.

The acyl having at most 6 carbon atoms is preferably formyl, acetyl, propionyl, butyryl or benzoyl but may also be valeryl, hexanoyl, acryloyl, crotonoyl or carbamoyl. The acyloxy is derived from an acyl of the values indicated above and preferably is formyloxy, acetyloxy, propionyloxy, butyryloxy or benzoyloxy.

The aryl may be the aryls as defined above, that is unsaturated carbocyclic or heterocyclic monocyclic or condensed rings, it being understood that the heterocyclics can contain one or more heteroatoms chosen from oxygen, nitrogen or sulfur and that when these heterocyclics contain more than one heteroatom, the heteroatoms of these heterocyclics can be identical or different.

Examples of such aryls are phenyl, naphthyl, thienyl such as 2-thienyl and 3-thienyl, furyl such as 2-furyl, pyridyl such as 3-pyridyl, pyrimidyl, pyrrolyl, thiazolyl, isothiazolyl, diazolyl, triazolyl, tetrazolyl, thiadiazolyl, thiatriazolyl, oxazolyl, oxadiazolyl and 3- or 4-isoxazolyl or heterocyclics containing at least one heteroatom chosen from sulfur, nitrogen and oxygen such as benzothienyl such as 3-benzothienyl, benzofuryl, benzopyrrolyl, benzimidazolyl, benzoxazolyl, thionaphthyl, indolyl and purinyl. The aryloxys have an aryl with the meaning indicated above and includes for example, phenoxy or pyridyloxy.

The carboxy(s) of the products of formula I can be salified or esterified by the various groups known to one skilled in the art such as with mineral bases such as an equivalent of sodium, potassium, lithium, calcium, magnesium or ammonium or organic bases such as methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine and N-methylglucamine.

The alkyls to form carbonylalkoxys such as methoxycarbonyl, ethoxycarbonyl, tertbutoxycarbonyl or benzyloxycarbonyl may be substituted by radicals chosen from halogens, hydroxyl, alkoxy, acyl, acyloxy, alkylthio, amino or aryl such as chloromethyl, hydroxypropyl, methoxymethyl, propionyloxymethyl, methylthiomethyl, dimethylaminoethyl, benzyl, phenethyl, chlorobenzyl, methoxybenzyl or trifluoromethylbenzyl.

The addition salts with mineral or organic acids of the products of formula I can be the salts formed with the following acids: hydrochloric acid, hydrobromic acid, hydroiodoic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmonosulfonic acids such as methanesulfonic acid, ethanesulfonic acid, propanesulfonic acid, alkyldisulfonic acids such as methmedisulfonic acid, $\alpha,\beta$-ethane-disulfonic acid, arylmonosulfonic acids such as benzenesulfonic acid and aryldisulfonic acid.

The alkyl, alkenyl, alkynyl, the monocyclic ring or condensed rings, and the aryl and aryloxy as defined above can be unsubstituted or have at least one substituent selected from the group consisting of halogens such as chloro or bromo, as in 2-bromoethyl or o-chloro-phenyl, —OH, alkyl such as lower alkyl like methyl, ethyl, isopropyl or tert-butyl, substituted alkyl such as trihaloalkyl as in trifluoromethyl or such as N-methylpyrrolyl; the substituted 3- or 4-isoxazolyl such as 3-aryl-5-methylisoxazol-4-yl, the aryl being phenyl or halophenyl, alkenyl such as vinyl or allyl, alkynyl, such as propargyl or ethynyl, aryl as defined above, either a monocyclic ring or condensed rings, carbocyclic or hetercyclic, it being understood that the heterocyclics as defined above can contain one or more heteroatoms chosen from oxygen, nitrogen or sulfur and that when these heterocyclics contain more than one heteroatom, the heteroatoms of these heterocyclics can be identical or different, this heterocyclic being able to be linked by a carbon atom or, if appropriate, by a nitrogen atom such as the substituted 3- or 4-isoxazolyl like 3-aryl-5-methylisoxazol-4-yl, the aryl being phenyl or halophenyl, arylalkyl in which the aryl is as defined above such as benzyl, cycloalkyl such as cyclopropyl, cyclopentyl or cyclohexyl and cycloalkenyl such as cyclohexenyl, these being optionally substituted such as dimethyl-1,3-cyclohexene; alkoxy as defined above such as methoxy, ethoxy, propoxy or isopropoxy as in methoxymethyl or 1-ethoxyethyl, substituted alkoxy such as trihaloalkoxy i.e., trifluoromethoxy, aryloxy, phenoxy, aralkoxy such as benzyloxy, mercapto, alkylthio such as methylthio or ethylthio, substituted alkylthio such as trihaloalkylthio like trifluoromethylthio, arylthio such as phenylthio, aralkylthio such as benzylthio, amino as in 2-aminoethyl, amino substituted by one or two members chosen from the alkyl, alkenyl, aryl and arylalkyl as defined above such as monoalkylamino like methylamino or ethylamino, dialkylamino like dimethylamino; a heterocyclic hydrocarbon ring containing 5 to 7 links or condensed rings containing 8 to 10 links, these being able to contain one or more different or identical heteroatoms chosen from oxygen, nitrogen or sulfur and being optionally substituted, this heterocyclic being able to be linked by a carbon atom or by a nitrogen atom, for example piperidinyl, morpholinyl, piperazinyl, methylpiperazinyl, nitro, cyano, azido, carboxy, salified or esterified carboxy such as methoxycarbonyl or ethoxycarbonyl, formyl, acyl such as acetyl, propionyl or benzoyl, acyl substituted by an amino as defined above or by a cyclic ring linked to the acyl by a nitrogen atom, this cyclic ring being able to contain optionally one or more heteroatoms chosen from nitrogen, oxygen or sulfur and as defined and their non-phthalimido; acylamido such as acetamido or benzamido; alkoxycarbonylamino such as methoxycarbonylamino or ethoxycarbonylamino; or aralkoxycarbonylmino such as benzyloxycarbonylamino.

In the products of formula I

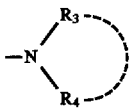

preferably when $R_3$ and $R_4$ form, together with the nitrogen atom to which they are linked a heterocycle, one of the following groups pyrrolyl, imidazolyl, pyridyl, pyrazinyl, pyrimidyl, indolyl, indolinyl, purinyl, quinolyl, pyrrolidinyl, piperidyl, piperidino, morpholino, piperazinyl; these being optionally substituted by the substituents mentioned above and in particular by at least one member of the group consisting of chlorine, fluorine, methyl, ethyl, isopropyl, tert-butyl, methoxy, ethoxy, propoxy, benzoyl, methoxycarbonyl and ethoxycarbonyl such as methylpiperazinyl, thylpiperazinyl, propylpiperazinyl, phenylpiperazinyl or benzylpiperazinyl. In these two latter, the phenyl and benzyl can be substituted as indicated above in the aryl, arylalkyl and arylalkenyl such as chlorophenyl or trifluorophenyl.

When $R_3$ and $R_4$ form, on the nitrogen atom to which they are linked, monoalkyl- or dialkylaminos, $R_3$ and $R_4$ are alkyl of 1 to 6 carbon atoms and particularly methyl, ethyl, isopropyl, trifluoromethyl, pentafluoroethyl, hydroxymethyl, hydroxyethyl, methoxymethyl, methoxyethyl, ethoxyethyl. The alkenyl as defined above is preferably vinyl and allyl and the acyl is preferably chosen from acetyl, propionyl, butyryl, valeryl or carbamoyl. The aryl or arylalkyl are as defined above, carbocyclic or heterocyclic and particularly phenyl, benzyl, phenethyl, naphthyl, indolyl, indolinyl, thienyl, furyl, pyrrolyl, pyridyl, pyrrolidinyl, piperidino, morpholino, piperazinyl, these being able to be substituted by one or more members as defined above such as methylpiperazinyl, fluoromethylpiperazinyl, ethylpiperazinyl, propylpiperazinyl, phenylpiperazinyl or benzylpiperazinyl.

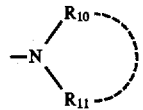

as defined above in $R_1$ preferably has the values indicated above for

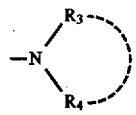

when $R_{10}$ and $R_{11}$ form, together with the nitrogen atom to which they are linked, a heterocycle, or when $R_{10}$ and $R_{11}$ form on the nitrogen atom to which they are linked monoalkyl- or dialkylamino.

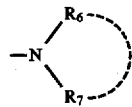

and

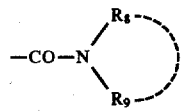

preferably are those in which $R_6$, $R_7$, $R_8$ and $R_9$ have the meanings previously indicated for alkyl, alkoxy, acyloxy, acyl or salified or esterified carboxy.

Among the preferred compounds of formulae I and $I_A$ are those wherein the alkyl, alkenyl and alkynyl and the monocyclic rings are condensed rings, aryl and aryloxy are substituted with at least one member of the group consisting of halogens, hydroxyl, cyano, mercapto, nitro, acyl and acyloxy of 1 to 6 carbon atoms, free, salified or esterified carboxy, alkoxycarbonyl; alkoxy of 1 to 6 carbon atoms; alkyl, alkenyl, alkynyl, alkylthio, cycloalkyl, cycloalkenyl, heterocyclic hydrocarbons, aryl, aryloxy, arylthio, phenylalkyl, phenylalkoxy optionally substituted by one or more substituents chosen from halogens, hydroxyl, trifluoromethyl, nitro, akyl, alkenyl, aryl, alkoxy and acyl of at most 6 carbon atoms, free, salified or esterified carboxy, acylamido in which the acyl contains at most 6 carbon atoms, carbamoyl and amino, these being optionally substituted on the nitrogen atom by one or two identical or different members chosen from hydroxyl, alkyl and alkoxy of 1 to 6 carbon atoms; acylamido in which the acyl contains at most 6 carbon atoms; carbamoyl and amino optionally substituted on the nitrogen atom by one or two identical or different members chosen from hydroxyl, alkyl, alkenyl and alkoxy of 1 to 6 carbon atoms; the said products of formula $I_A$ and I being in all the possible racemic, enantiomeric and diastereoisomeric isomer forms, as well as the addition salts with mineral and organic acids of the said products of formula $I_A$ and I.

In the products of formula $I_A$ and I, follows: the halogen preferably is chlorine, but can also be fluorine, bromine or iodine, the cycloalkyls preferably cyclopropyl, cyclopentyl or cyclohexyl and the cycloalkenyl preferably is cyclopentenyl and cyclohexenyl optionally substituted as indicated above such as dimethyl-1,3-cyclohexenyl. The phenylalkyl preferably is benzyl or phenethyl and the phenylalkoxy preferably is benzyloxy and phenethoxy. The acylamido preferably is acetamido or benzoylamido.

Examples of alkyl substituted by an aryl are benzyl, diphenylmethyl, triphenylmethyl, naphthylmethyl, indenylmethyl, thienylmethyl such as 2-thienylmethyl, furylmethyl such as furfuryl, pyridylmethyl, pyrimidylmethyl or pyrrolylmethyl, it being understood that in the non-exhaustive list of examples as mentioned above, the alkyl can be represented also as ethyl, propyl or butyl such as, for example, in phenethyl.

Examples of alkenyl substituted by an aryl are those of arylalkyl in which the alkyl is replaced by alkenyl such as phenylvinyl or phenylallyl, it being understood that the phenyl can be replaced quite as equally by naphthyl or pyridyl or also by one of the aryls as defined above as defined above.

The carbocyclic or heterocyclic aryl as defined above preferably is phenyl, benzyl, phenethyl, naphthyl, indolyl, indolizinyl, thienyl, furyl, pyrrolyl or pyridyl.

The heterocyclic aliphatic hydrocarbon as defined above preferably is pyrrolidinyl, piperidino, morpholino or piperazinyl optionally substituted by one or more members as defined above such as methylpiperazinyl, fluoromethylpiperazinyl, ethylpiperazinyl, propylpiperazinyl, phenylpiperazinyl or benzylpiperazinyl.

The amino and carbamoyl designate members in which the nitrogen atom can be substituted by one or two members chosen from the substituents as defined previously. By way of example and in a non-exhaustive fashion, substituted carbamoyl includes lower N-monoalkyl carbamoyl such as N-methylcarbamoyl, N-ethylcarbamoyl; lower N,N-dialkylcarbamyl such as N,N-dimethylcarbamoyl, N,N-diethylcarbamoyl; N-(lower hydroxyalkyl) carbamoyl such as N-(hydroxymethyl)carbamoyl, N-(hydroxyethyl) carbamoyl; lower carbamoylalkyl such as carbamoylmethyl or carbamoylethyl.

The substituted amino can be monoalkyl- or dialkylamino in which the alkyl is chosen from methyl, ethyl or isopropyl. Examples of such a substituted amino are given in the experimental part hereafter.

A particular subject of the invention are the products of formula $I_A$ as defined above corresponding to the formula

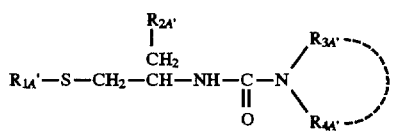

wherein $R'_{1A}$ is hydrogen or $—R'_{5A}—CO—$ or

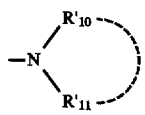

or $R'_{5A}$ is selected from the group consisting of phenyl, cycloalkyl, cycloalkenyl, alkyl and alkenyl of up to 6 carbon atoms, all optionally substituted, $R'_{10}$ and $R'_{11}$ together with the nitrogen to which they are attached form a member of the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, methylpiperazinyl, piperidyl, oxazolyl, morpholinyl and thiomorpholinyl, azepinyl and indolyl, all optionally substituted by at least one member of the group consisting of halogen, hydroxyl, mercapto, trifluoromethyl, alkyl, alkenyl, alkynyl, alkylthio, alkoxy and phenyl optionally substituted by at least one member of the group consisting of halogen, —$CF_3$, hydroxyl and alkyl and alkoxy of 1 to 6 carbon atoms, or $R_{10}'$ and $R_{11}'$ are individually selected from the group consisting of halogen, alkyl, alkenyl or alkynyl of up to 6 carbon atoms and optionally substituted phenyl, benzyl, naphthyl, indenyl, imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomopholinyl, azepinyl, indolyl, all optionally substituted by at least one member of the group consisting of halogen, hydroxyl, mercapto, trifluoromethyl and alkyl, alkenyl, alkynyl, alkylthio and alkoxy of up to 6 carbon atoms, $R_2'$ is selected from the group consisting of phenyl, naphthyl, benzyl, phenethyl, indolyl, cycloalkyl and cycloalkenyl, all optionally substituted, $R_{3A}$, and $R_{4A}$, form with the nitrogen atom to which they are attached a member of the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepinyl and indolyl, all optionally substituted by at least one member of the group consisting of halogen, hydroxyl, trifluoromethyl, alkyl, alkenyl, alkynyl, alkoxy and phenyl optionally substituted by at least one member of the group consisting of halogen, trifluoromethyl, hydroxyl and alkyl and alkoxy of up to 6 carbon atoms and optionally substituted by a phenyl, or $R_{3A}$, and $R_{4A}$, are individually selected from the group consisting of hydrogen, hydroxyl, alkoxy, acyloxy or acyl of up to 6 carbon atoms, salified or esterified carboxy, cyano, alkyl, alkenyl or alkynyl of up to 6 carbon atoms and optionally substituted, phenyl, benzoyl, naphthyl, indenyl, imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl, thiomorpholinyl, azepinyl, diazepinyl, benzodiazepinyl and indolyl, all optionally substituted by at least one member of the group consisting of halogen, hydroxyl, trifluoromethyl and alkoxy and alkyl of 1 to 6 carbon atoms optionally substituted by at least one member of the group consisting of halogen, hydroxyl, alkyl, alkoxy and carboxy, free, salified or esterified by alkyl, aryl or arylalkyl,

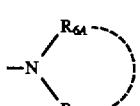

or

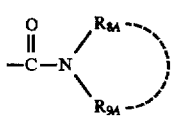

$R_{6A'}$, $R_{7A'}$, $R_{8A'}$ and $R_{9A'}$ are individually selected from the group consisting of hydrogen, hydroxyl, alkyl, alkoxy, acyloxy and acyl of up to 6 carbon atoms, free, salified or esterified carboxy, phenyl, benzyl, phenethyl, azepinyl, piperidyl, morpholinyl, pyrrolidinyl and piperazinyl or $R_{6A'}$ and $R_{7A'}$ and/or $R_{8A'}$ and $R_{9A'}$ form with the nitrogen atom to which they are attached a member of the group consisting of imidazolyl, pyrrolyl, pyrrolinyl, pyrrolidinyl, pyridyl, piperidinyl, pyrimidinyl, pyridzinyl, pyrazinyl, piperazinyl, phenylpiperazinyl, piperidyl, oxazolyl, morpholinyl, thiomorpholinyl, azepinyl and indolyl, all optionally substituted by at least one member of the group consisting of halogen, hydroxyl, trifluoromethyl and alkyl and alkoxy of 1 to 6 carbon atoms, it being understood that the optional substituent(s) that can be carried by $R_{1A'}$, $R_{2A'}$ and $R_{5A'}$ are selected from the group consisting of halogen, hydroxyl, cyano, nitro, acyl and acyloxy of up to 6 carbon atoms, benzoyl, free, salified or esterified carboxy, alkoxy of 1 to 6 carbon atoms, alkyl, alkenyl, cyclopentyl, cyclohexyl, cyclopentenyl, cyclohexenyl, phenyl, naphthyl, indolyl, phenoxy, benzyl, phenethyl and benzyloxy, all optionally substituted by at least one member of the group consisting of halogen, hydroxyl, trifluoromethyl, nitro and alkyl, alkenyl and alkoxy of up to 6 carbon atoms, formyl, acetyl, benzoyl, free, salified or esterified carboxy, acetamido, benzoylamido, carbamoyl and amino, all optionally substituted on the nitrogen atom by one or two members of the group consisting of hydroxyl, methyl, ethyl, propyl, methoxy, ethoxy and propoxy; acylamido in which the acyl has up to 6 carbon atoms; carbamoyl and amino optionally substituted on the nitrogen atom by one or two members of the group consisting of hydroxyl and alkyl, alkenyl, alkoxy and acyl of up to 6 carbon atoms; the said products of formula $I'_A$ being in all the possible racemic, enantiomeric and diastereoisomeric isomer forms and their non-pharmaceutically acceptable addition salts.

Another preferred group of compounds of the invention have the formula

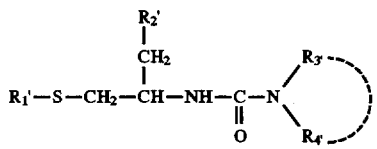

wherein $R_1'$ is selected from the group consisting of hydrogen, $R_5'$ —CO—

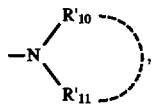

is selected from the group consisting of phenyl, cycloalkyl, cycloalkenyl, alkyl and alkenyl of up to 6 carbon atoms, all optionally substituted, $R_{10}'$ and $R_{11}'$ form with the nitrogen atom to which they are attached at least one member of the group consisting of imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl, thiomorpholinyl, azepinyl and indolyl, all optionally substituted by at least one member of the group consisting of halogen, hydroxyl, trifluoromethyl, alkyl, alkoxy and phenyl optionally substituted by at least one member of the group consisting of halogen, trifluoromethyl, hydroxy, alkyl and alkoxy up to 6 carbon atoms, or $R_{10}'$ and $R_{11}'$ are individually selected from the group consisting of hydrogen, alkyl, alkenyl and alkynyl of up to 6 carbon atoms and optionally substituted, phenyl, benzoyl, naphthyl, indenyl, imidazolyl, pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl, thiomorpholinyl, azepinyl and indolyl, all optionally substituted by at least one member of the group consisting of halogen, hydroxyl, trifluoromethyl and alkyl and alkoxy of 1 to 6 carbon atoms, $R_2'$ is selected from the group consisting of phenyl, naphthyl, benzyl, phenethyl, indolyl, cyoloalkyl and cycloalkenyl, all optionally substituted, $R_3'$ and $R_4'$ form with the nitrogen atom to which they are linked at least one member of the consisting of imidazolyl,.pyrrolyl, pyrrolinyl, pyrrolidinyl, pyridyl, piperidinyl, pyrimidinyl, pyridazinyl, pyrazinyl, piprazinyl, phenylpiperazinyl, piperidyl, oxazolyl, morpholinyl, thiomorpholinyl, azepinyl and indolyl, all optionally substituted by at least one member of the group consisting of halogen, hydroxyl, trifluoromethyl, alkyl, alkoxy and phenyl optionally substituted by at least one member of group consisting of halogen, trifluoromethyl, hydroxyl and alkyl and alkoxy of 1 to 6 carbon atoms, or $R_3'$ and $R_4'$ are individually selected from the group consisting of hydrogen, hydroxyl, alkoxy, acyloxy and acyl of up to 6 carbon atoms, salified or esterified carboxy, cyano, alkyl, alkenyl and alkynyl of up to 6 carbon atoms and optionally substituted, phenyl, benzoyl, naphthyl, indenyl, imidazolyl pyrrolyl, pyrrolinyl, pyrrolidinyl, pyridyl, piperidinyl, pyrimidinyl, pyridazinyl, pyrazinyl, piperazinyl, phenylpiperazinyl, piperidyl, oxazolyl, morpholinyl and thiomorpholinyl, azepinyl and indolyl, all optionally substituted by at least one member of the group consisting of halogen, hydroxyl, trifluoromethyl and alkoxy and alkyl of 1 to 6 carbon atoms,

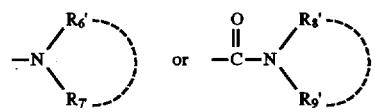

$R_6'$, $R_7'$, $R_8'$ and $R_9'$ are individually a member of the group consisting of hydrogen, hydroxyl, alkyl, alkoxy, acyloxy and acyl of up to 6 carbon atoms, free, salified or esterified carboxy, phenyl, benzyl, phenethyl, azepinyl, piperidyl, morpholinyl, pyrrolidinyl and piperazinyl or $R'_6$ and $R'_7$ and $R'_8$ and $R'_9$ form with the nitrogen atom to which they are attached a member of group consisting of imidazolyl, pyrrolyl, pyrrolinyl, pyrrolidinyl, pyridyl, piperidinyl, pyrimidinyl, pyridazinyl, pyrazinyl, piperazinyl, phenyl-piperazinyl, piperidyl, oxazolyl, morpholinyl, thiomorpholinyl, azepinyl and indolyl, all optionally substituted by at least one member of group consisting of halogen, hydroxyl, trifluoromethyl and alkyl and alkoxy of 1 to 6 carbon atoms, it being understood that the optional substituent or substituents, that can be carried by $R_1'$, $R_2'$ and $R_5'$ are a member of the group consisting of halogen, hydroxyl, cyano, nitro, acyl and acyloxy of up to 6 carbon atoms, benzoyl, free, salified or esterified carboxy, alkoxy of 1 to 6 carbon atoms; alkyl, alkenyl, cyclopentyl, cyclohexyl, cyclopentenyl, cyclohexenyl, phenyl, naphthyl, indolyl, phenoxy, benzyl, phenethyl and benzyloxy, all optionally substituted by at least one members of the group consisting of halogen, hydroxyl, trifluoromethyl, nitro, alkyl, alkenyl, alkoxy of up to 6 carbon atoms, formyl, acetyl, benzoyl, free, salified or esterified carboxy, acetamido, benzoylamino, carbamoyl and amino, all optionally substituted on the nitrogen atom by one or two member of the group consisting of hydroxyl, methyl, ethyl, propyl, methoxy, ethoxy and propoxy; acylamido in which the acyl has up to 6 carbon atoms; carbamoyl and amino optionally substituted on the nitrogen atom by one or two members of the group consisting of hydroxyl and alkyl, alkenyl, alkoxy and acyl of up to 6 carbon atoms; the said products of formula $I'$ being in all the possible racemic, enantiomeric and diastereoisomeric isomer forms and their non-toxic, pharmaceutically acceptable acid addition salts.

Among the preferred compounds of formula $I'_A$ are those wherein $R_1'$ is hydrogen or acetyl, those wherein $R_2'$ is phenyl, those wherein $R_3'$ and $R_4'$ form with the nitrogen atom to which they are attached a member of the group consisting of piperidinyl, morpholinyl, dimethylmorpholinyl, thiomorpholinyl, pyrrolidinyl, azepinyl, diazepinyl optionally substituted on the second nitrogen atom by alkyl of 1 or 2 carbon atoms, piperazinyl optionally substituted on the second nitrogen atom either by phenyl optionally substituted by halogen or trifluoromethyl or by alkyl, alkenyl or alkynyl up to 4 carbon atoms optionally substituted by phenyl or acyl or by acyl of up to 6 carbon atoms, or $R_3'$ and $R_4'$ are individually selected from the group consisting of hydrogen, hydroxy, phenyl, phenyl substituted by carboxy, piperidinyl, optionally substituted on the nitrogen atom by benzyl, piperazinyl optionally substituted on the second nitrogen atom by alkyl of 1 or 2 carbon atoms, carbamoyl, alkoxy of 1 to 4 carbon atoms, alkyl of 1 to 4 carbon atoms optionally substituted by at least one member of the group consisting of hydroxyl, alkoxy, free, salified or esterified carboxy, amino, alkylamino, dialkylamino, phenyl, morpholinyl, alkylthio of 1 to 4 carbon atoms, optionally substituted by a free, salified or esterified carboxy, optionally substituted benzodiazepine, the said products of formula $I_A$ being in all the possible racemic, enantiomeric and diastereoisomeric isomer forms and their acid addition salts.

The more preferred compounds of formula I' are those wherein $R_1'$ is hydrogen or acetyl, $R_2'$ is phenyl and $R_3'$ and $R_4'$ form with the nitrogen atom to which they are attached a member of the group consisting of piperidinyl, morpholinyl, dimethylmorpholinyl, thiomorpholinyl, pyrrolidinyl, azepinyl, piperazinyl optionally substituted on the second nitrogen atom by alkyl of 1 or 2 carbon atoms and phenyl optionally substituted by halogen or trifluoromethyl, or $R_3'$ and $R_4'$ are individually selected from the group consisting of hydrogen, hydroxyl, phenyl, carbamoyl, alkoxy of 1 to 4 carbon atoms, alkyl of 1 to 4 carbon atoms optionally substituted by at least one member of the group consisting of hydroxyl, alkoxy, free or salified or esterified carboxy, the said products of formula I' being in all the possible racemic, enantiomeric and diastereoisomeric isomer forms and their addition salts.

Specific preferred compounds of the invention are (±) 4-methyl-N-[2-mercapto-1-benzyl-ethyl]-1-piperazinecarboxamide hydrochloride, (±) N-[2-mercapto-1-benzyl-ethyl]-4-morpholine-carboxamide, (±) N-[2-mercapto-1-benzyl-ethyl]-1-pyrrolidine-carboxamide, (±) N-[[[2-mercapto-1-benzyl-ethyl]-amino]-carbonyl]-glycine, N,N,-bis-(2-methoxyethyl)-N'-[2-mercapto-1-benzyl-ethyl]-urea, (±) cis-2,6-dimethyl-N-[2-mercapto-1-benzyl-ethyl]-4-morpholinecarboxamide (isomer A), (±) N-[2-mercapto-1-benzyl-ethyl]-4-thiomorpholine-carboxamide, (±) N-[2-mercapto-1-benzyl-ethyl]-N'-methoxy urea, (±) N-hydroxy-N'-[2-mercapto-1-benzyl-ethyl]-N-methyl urea, (±) N-(1-mercaptomethyl)-2-phenethyl)-4-methyl-1-piperazine acetamide and their non-toxic, pharmaceutically acceptable acid addition salts.

The novel process of the invention for the preparation of compounds of formula $I_A$ wherein n=0 comprises reacting a compound of the formula

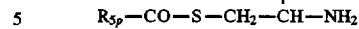

II $$R_{5p}-CO-S-CH_2-CH-NH_2$$ with $R_{2p}$/Ap above wherein $R_{5p}$, $R_{2p}$ and Ap have the meanings indicated above for $R_5$, $R_2$ and A respectively in which the optional reactive functions are optionally protected by protective groups with a reagent such as phosgene or thiophosgene to obtain respectively the isocyanate or the isothiocyanate of the formula

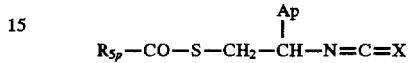

III $$R_{5p}-CO-S-CH_2-CH-N=C=X$$

in which $R_{5p}$, $R_{2p}$ and AP have the above meanings and X is oxygen or sulfur, reacting the latter with a compound of the formula

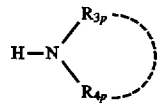

IV wherein $R_{3p}$ and $R_{4p}$ have the above meanings for $R_3$ and $R_4$ respectively in which the optional reactive functions are optionally protected by protective groups to obtain a product of the formula

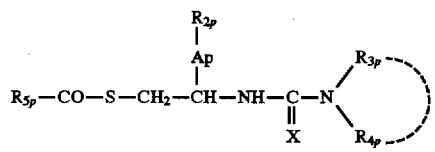

V wherein $R_{5p}$, $R_{2p}$, Ap, $R_{3p}$, $R_{4p}$ and X have the above meanings, subjecting the latter, if necessary and if desired, to an elimination reaction of the $R_{5p}$—CO— to obtain a product of the formula

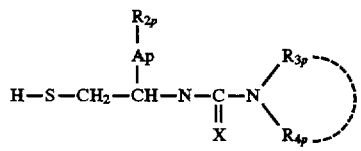

VI wherein $R_{2p}$, Ap, $R_{3p}$, $R_{4p}$ and X have the above meanings.

The process of the invention to produce compounds of formula $I_A$ wherein X is oxygen and n is other than zero comprises reacting a compound of the formula

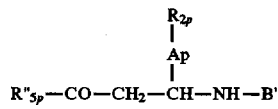

II'

$$R''_{5p}-CO-CH_2-CH-NH-B'$$

wherein B' is hydrogen or protective group of the amine function and $R''_5$ is alkyl of 1 to 4 carbon atoms substituted by an

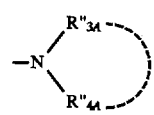

wherein $R''_{3A}$ and $R''_{4A}$ have the value indicated above for $R_{3A}$ and $R_{4A}$ respectively, if appropriate, of an elimination agent of the protective group carried by the amine function, then to the action of an alkaline agent to obtain by molecular transposition a product of the formula

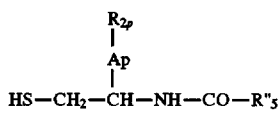

VII wherein $R_{2p}$, Ap and $R''_5$ have the above meanings, treating the products of formulae V, VI and VII, if desired and if necessary, to one or several of the following reactions in any order:

an elimination reaction of the protective groups that can be carried by the protected reactive functions, a salification reaction by a mineral or organic acid to obtain the corresponding salt, a reduction reaction of the esterified carboxy function into an alcohol function, a saponification reaction of the ester function into an acid function, a conversion reaction of the cyano function into an acid function, a conversion reaction of the alkoxy function into a hydroxyl function, an esterification, salification or carbamoylation reaction of the acid function, an esterification reaction of the thiol function by an acid or an acid function, or by an isocyanate or by carbamoyl chloride, the said products of formula I thus obtained being in all the possible racemic, enantiomeric and diastereoisomeric isomer forms.

Under the preferred conditions for implementing the invention, the compound of formula II is subjected to the action of a chloroformate such as and preferably trichloromethyl or diphosgene chloroformate to obtain the corresponding isocyanate of formula III in which X is oxygen, the compound of formula II is subjected to the action of a sulfur derivative such as and preferably thiophosgene to obtain the corresponding isothiocyanate of formula III in which X is sulfur. The reaction for obtaining the product of formula III is carried out by mixing the compound of formula II with the corresponding reagent such as phosgene or thiophosgene in a solvent such as toluene or methylene chloride, the mixture being refluxed for a period of about one hour and half.

The addition reaction of the compound of formula IV with the product of formula III to obtain the corresponding product of formula V is carried out by placing the product of formula III in a solvent such as methylene chloride or toluene in the presence of the compound of formula IV, the mixture being preferably cooled down to a temperature of about 0° C., then stirred at ambient temperature for a period of about two hours. If necessary and if desired, the product of formula V can be subjected to an elimination reaction of the $R_{5p}$—CO acyl to obtain the corresponding product of formula VI. The elimination reaction of the acyl can be obtained by placing the product of formula V in a solvent such as tetrahydrofuran or methylene chloride in the presence of hydrazine hydrate preferably at a temperature of about 0° C. for a period of about one hour or also in an acid or alkaline medium.

The elimination of the protective group that can be carried by the amine function of the product of formula II is carried out under the usual conditions known to one skilled in the art as indicated below. Trifluoroacetic acid is preferably used. The alkaline agent responsible for the molecular transposition can be a mineral base such as sodium hydroxide or potassium hydroxide, an alcoholate such as sodium methylate or ethylate or a carbonate such as sodium bicarbonate.

Depending upon the values of $R_{5p}$, $R_{2p}$, Ap, $R_{3p}$ or $R_{4p}$, the products of formulae V, VI and VII constitute or do not constitute the products of formula $I_4$. The various reactive functions that can be carried by certain compounds of the reactions defined above can, if necessary, be protected. For example, the hydroxyl, acyl, free carboxy or amino and monolkylamino can be protected by the appropriate protective groups.

The following non-exhaustive list of examples of protection of the reactive functions can be mentioned: the hydroxyl can be protected by alkyl, trimethylsilyl, dihydropyran, methoxymethyl or tetrahydropyrannyl and the amino can be protected by acetyl, trityl, benzyl, tert-butoxycarbonyl, phthalimido or other groups known in the chemistry of the peptides. The acyl such as formyl can be protected in the form of cyclic or non-cyclic ketals such as dimethyl- or diethylketal or ethylenedioxy and the acid functions of the products can be, if desired, amidified by a primary or secondary amine in the presence of methylene chloride in 1-ethyl-3-(dimethylaminopropyl) carbodiimide hydrochloride at ambient temperature. The carboxy can be protected in the form of esters formed with easily cleavable esters such as benzylic or terbutylic esters or esters known in the chemistry of the peptides.

The elimination of these protective groups is carried out under the usual conditions known to one skilled in the art, notably acid hydrolysis carried out with an acid such as hydrochloric acid, benzene sulfonic acid or p-toluene sulfonic acid, formic acid or trifluoroacetic acid. The phthalimido group is eliminated by hydrazine. A list of various protective groups which can be used will be found for example in the Patent BF 2,499,995.

The products described above can, if desired, be subjected to salification reactions with a mineral or organic acid carried out under the usual methods known to one skilled in the art to obtain the corresponding salt.

The optional esterified carboxy functions of the products can be, if desired, reduced to an alcohol function by methods known to a man of the art and notably by lithium aluminium hydride in a solvent such as tetrahydrofuran or dioxane or ethyl ether. The optional conversions of the ester function into an acid function of the products can be, if desired, carried out under the usual known conditions, especially by acid or alkaline hydrolysis with sodium hydroxide or potassium hydroxide in an alcoholic medium such as methanol or by hydrochloric acid or sulfuric acid.

The optional cyano functions of the products can be, if desired, converted into an acid function by the usual known conditions such as by a double hydrolysis carried out in an acid medium such as a mixture of sulfuric acid, glacial acetic acid and water, these three compounds being preferably in equal proportions, or also in a mixture of sodium hydroxide, ethanol and water at reflux.

The optional alkoxy functions, such as methoxy, of the above-described products can be, if desired, converted into an alcohol function by the usual known conditions such as by boron tribromide in a solvent such as methylene chloride, by pyridine hydrobromide or hydrochloride or also by hydrobromic acid or hydrochloric acid in water or acetic acid at reflux.

The optional acid functions of the products can be, if desired, esterified, salified or also amidified by the usual known conditions for example by the action on the acid or an activated form of the latter of an alcohol or of an amine.

The optically active form of the products of formula I can be prepared by resolving the racemics by the usual method.

The novel analgesic compositions of the invention are comprised of an analgesically effective amount of at least one compound of formula $I_A$ and their non-toxic, pharmaceutically acceptable acid addition salts and an inert pharmaceutical carrier. The compositions may be in the form of tablets, dragees, capsules, granules, suppositories, injectable solutions, suspensions, ointments, creams, gels and aerosols.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, and preservatives.

The compositions also have very useful enkephalinase-inhibiting properties as well as a very good analgesic activity. They also have psychotropic properties and notably anti-depressive and anxiolytic properties. Enkephalinase is a dipeptidylcarboxpeptidase which specifically hydrolyses methionine and leucine enkephaline between the third and fourth amino acid, thus releasing a tripeptide TYR-GLY-GLY (Swerts et al., Europ. J. Pharmacol. (1979); Vol. 57, p. 279). Enkephalinase thus participates directly in the degrading of enkephalines, endogenic natural ligands of the opiate receptors. The compositions of the invention, which delay the degradation of the enkephalines, therefore stimulate the organism's defense reactions against pain.

Some of the compounds of the invention are inhibitors of neutral endopeptidase EC 3.4.24.11. This enzyme is implicated particularly in the degradation of enkephalines and of the auricular natriuretic peptide (or ANF). ANF is a powerful vasodilatory, diuretic and natriuretic peptide and the inhibition of neutral endepeptidase EC 3.4.24.11 by these compositions can thus lead to a potentialization of the biological effects of ANF. Some compounds of the invention lead particularly to hemodynamic, diuretic and natriuetic effects.

Particularly useful for the compositions of the invention are those of formulae I and I' in their various isomeric forms and their acid addition salts.

The compositions are useful in the treatment of muscular, articular and nervous pains, rheumatic affections, toothaches, shingles and migraines, as well as in the treatment of inflammatory illinesses, notably osteoarthritis, lumbagos and as a complementary treatment in feverish and infectious conditions. They can also be used to treat depressive conditions.

Some compositions of the invention are useful in the treatment of cardiac insufficiency, renal insufficiency, hypertension combined or not with hyperreninemia, hyperaldosteronism, oedemas of various origins, glaucoma and also have a therapeutic use in the treatment of gastrointestinal disorders (particularly diarrhoea and irritable colon) as well as cognitive disorders.

The novel method of relieving pain in warm-blooded animals, including humans, comprises administering to warm-blooded animals an analgesically effective amount of at least one compound of formula $I_A$ and their non-toxic, pharmaceutically acceptable acid addition salts. The compounds may be administered orally, rectally, parenterally or topically to the skin or mucous membrane. The usual daily dose is to mg/kg depending upon the specific compounds used, the conditions treated and the method of administration.

The starting compounds of the formula

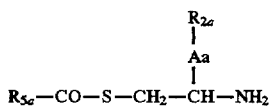

II' wherein $R_{5a}$ is acetyl, Aa is methylene and $R_{2a}$ is phenyl can be prepared as described in Patent Application No. PCT/FR87/00367.

The present invention also relates to a novel preparation process for the starting products of formula II comprising reacting a compound of the formula

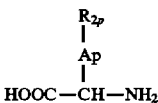

IIa wherein $R_{2p}$ and Ap have the above meanings for $R_2$ and A respectively in which the optional reactive functions are optionally protected by protective groups with a reducing agent of the acid function to obtain the corresponding alcohol of the formula

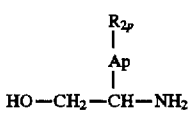

IIb wherein $R_{2p}$ and Ap have the above meanings, cyclizing the latter with a carbonylated derivative to obtain the corresponding oxazolidone of the formula

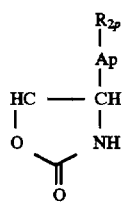

IIc wherein $R_{2p}$ and Ap have the above meanings, subjecting the latter to the action of a protective agent to obtain a product of the formula

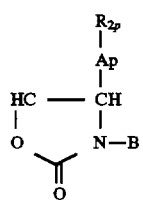

IId wherein $R_{2p}$ and Ap have the above meanings and B is a protective group of the amine, reacting the latter with a compound of the formula

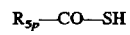

IIe wherein $R_{5p}$ has the above meaning for $R_5$ in which the optional reactive functions are optionally protected by protective groups to obtain a compound of the formula

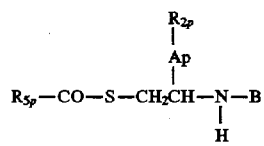

IIf wherein $R_{2p}$, $R_{5p}$, Ap and B have the above meanings, subjecting the latter if desired, to an elimination reaction of B, the said products of formula II being in all the possible racemic, enantiomeric and diastereoisomeric isomer forms.

Under the preferred conditions for the above process, the compound of formula IIa is subjected to the action of a reducing agent of the acid function by the usual known methods such as in the presence of lithium aluminium hydride in a solvent such as tetrahydrofuran. The compound of formula IIb thus obtained can be cyclized into the corresponding oxazolidone in the presence of carbodiimidazole in a solvent such as tetrahydrofuran and the mixture is preferably taken to a temperature of about 40° to 60° C. for a period of about two hours with stirring.

The oxazolidone of formula IIc can be subjected to the action of a blocking agent B of the hydrogen such as ditertbutyloxcarbonyl oxide in solution in a solvent such as acetonitrile preferably in the presence of a catalyst such as DMAP, the mixture preferably being stirred for a variable period of time of about 18 hours at ambient temperature. The oxazolidone thus blocked of formula IId is reacted with a compound of formula IIe activated in the form a sodium or potassium salt such as potassium thioacetate, preferably in the presence of water in a solvent such as dimethylformamide. The mixture is preferably taken to a temperature of about 100° C. for a period of about two hours. The compound of formula IIf can be subjected to an elimination reaction of the blocking group B such as butyloxycarbonyl by the usual known methods such as by bubbling in a solvent such as ethyl acetate or ether, preferably with stirring for about two hours and in the presence of an excess of gaseous hydrogen chloride to obtain the corresponding compound of formula II or also by trifluoroacetic acid for example in methylene chloride.

The compound of formula IIa can be a natural amino acid such as phenylalanine, tyrosine or tryptophane, which can be found in the form of a product commercially available for example from FLUKA. The other products of formula IIa can be prepared by known methods using for example glycine as the starting product, or can be prepared by the usual known methods.

The reagents acting on the starting products of formula II such as diphosgene or thiophosgene to obtain the corresponding products of formula III can be found in the form of a product commercially available for example from FLUKA.

Finally, a subject of the present invention is, as new intermediate products necessary for the preparation of products of formula I, the compounds of formula III.

In the following examples, there are described several preferred embodiments to illustrate the invention. However, it should be understood that the invention is not intended to be limited to the specific embodiments.

Preparation of: S-(2-isocyanato-3-phenyl propyl)-ethanethioate

STEP A: (+) beta-amino benzenepropanol 30 g of (D,L) phenylalanine were added to a stirred mixture of 18.4 g of lithium aluminium hydride and 1000 ml of tetrahydrofuran without exceeding 30° C. The mixture was heated for 20 minutes at reflux, cooled down and 18.4 ml of water, then 18.4 ml of a 15% solution of sodium hydroxide and 55.2 ml of water were added. The insolubles were filtered off and washed with tetrahydrofuran. The filtrate was dried and evaporated to dryness under reduced pressure. The residue was crystallized from a mixture of ethyl acetate and hexane to obtain 21.2 g of the desired product melting at 68° C. to 71° C.

IR Spectrum (CHCl$_3$)

| OH | 3620 cm$^{-1}$ |
|---|---|
| NH$_2$ | 3370 cm$^{-1}$ |
| Aromatics | 1601–1495 cm$^{-1}$ |
| NH$_2$ def | 1580 cm$^{-1}$ |

STEP B: (+) 4-(phenylmethyl)-2-oxazolidinone 2.4 g of carbonyldiimidazole were added to a solution of 1.51 g of the product of Step A in 50 ml of tetrahydrofuran and the mixture was stirred for 2 hours at 40 to 45° C. and then concentrated under reduced pressure. The residue was chromatographed on silica, eluant: methylene chloride to obtain 1.2 g of the desired product melting at 66° C.

IR Spectrum (CHCl$_3$)

| =C—NH | 3452 cm$^{-1}$ |
|---|---|
| C=O | 1760 cm$^{-1}$ |
| Aromatics | 1495 cm$^{-1}$ |

STEP C: (1,1-dimethyl ethyl (+) 2-oxo-4-(phenylmethyl)-3-oxazolidinecarboxylate 100 mg of 4-dimethylamino-pyridine and then 25.5 ml of ditertbutyl dicarbonate were added to a solution of 17.9 g of the product of Step B in 150 ml of acetonitrile and the mixture was stirred for 18 hours. The precipitate was separated out to obtain 11.4 g of the desired product melting at 119° C. By concentration of the mother liquors, another 3.7 g of the desired product were obtained and an additional 3.4 g of product were obtained by chromatography on silica of the dry extract of the filtrate.

NMR Spectrum CDCl$_3$ 250 MHz

| t-butyl | 1.58 ppm |
|---|---|
| C$_6$H$_5$—CH$_2$—CH = | 2.8 ppm |
| O—CH$_2$—CH—CH$_2$ = | 4.05 to 4.55 ppm |
| Aromatic | 7.15 ppm |

STEP D: (+) S-[2-[[((1,1-dimethyl-ethoxy)-carbonyl)-amino]-3-phenyl-propyl]-ethanethioate 3.42 g of potassium thioacetate and 0.180 ml of water were added to a solution of 2.77 g of the product of Step C in 28 ml of dimethylformamide and the mixture was heated for 150 minutes at 85° C. to 87° C. The mixture was poured into 150 ml of water and extracted with ether. The extracts were washed with water, dried, filtered and concentrated under reduced pressure. After chromatography on silica (eluant: methylene chloride—ethyl acetate 1-1), 2.6 g of the desired product melting at 68° C. to 70° C. were obtained.

NMR Spectrum ppm

| t.Bu | 1.40 ppm |
|---|---|
| S—CO—CH$_3$ | 2.36 ppm |
| the CH$_2$'s | 2.73 to 3.10 4.8 H |

| | |
|---|---|
| 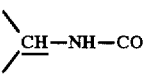CH—NH—CO | 3.98 ppm 1H<br>4.62 m 1H |
| 7.15 to 7.34 ppm approx. 6.5 H 4 aromatics | |

STEP E: (+) S-[2-amino-3-phenyl-propyl]-ethanethioate hydrochloride

Gaseous hydrogen chloride was bubbled through a solution of 1.5 g of the product of Step C in 30 ml of ethyl ether for 2 hours during which the temperature increased to 30° C. then stabilized at 10° C. When the bubbling through was completed, the mixture was stirred for 3 hours and the precipitate was separated out, washed with ether and dried under reduced pressure to obtain 0.78 g of the expected product melting at 40° C.

NMR Spectrum (CDCl₃ 250 MHz

| | |
|---|---|
| CH₃ | 2.40 ppm |
| 2 CH₂ | 3.0 to 3.5 ppm |
| NH₂—CH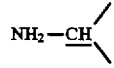 | 3.75 ppm |
| NH₂ | 8.6 ppm |
| Aromatic H's | 7.29 ppm |

STEP F: S-[2-isocyanato-3-phenyl-propyl]-ethanethioate

A mixture of 2.45 g of the product of Step E, 60 ml of toluene, 0.9 ml of trichloromethyl chloroformate (diphosgene) and 0.125 g of activated charcoal (acticarbon 3 SA) was heated at reflux for 90 minutes. After cooling down and filtering, the filtrate was washed with toluene and concentrated to dryness under reduced pressure to obtain 2.5 g of the desired product which was used as is in the start of the examples. After chromatography on silica, eluant: methylene chloride, 1.5 g of purified product were obtained.

IR Spectrum ( CHCl₃)

| | |
|---|---|
| N=C=O | 2265 cm⁻¹ |
| C=O | 1695 cm⁻¹ |
| Aromatic | 1600 cm⁻¹<br>1580 cm⁻¹<br>1496 cm⁻¹ |

EXAMPLE 1

S-[2-(3-methoxy-ureido)-3-phenyl-propyl]-ethanethioate 2.09 ml of triethylamine in solution in 20 ml of methylene chloride were added at 0° C. to a stirred mixture of 2.35 g of the isocyanate of Step F of the above preparation with 1.252 g of O-methylhydroxylamine hydrochloride and 100 ml of methylene chloride. The reaction mixture was stirred for 2 hours at ambient temperature and then poured into a mixture of water and 2N hydrochloric acid at pH 1. After decanting, the organic phase was washed with water, dried, filtered and evaporated to dryness to obtain 3 g of dry extract which was impasted in ether. After separating, 2 g of the desired product melting at 110° to 112° C. were obtained.

NMR Spectrum CDCl₃

| | |
|---|---|
| S—CO—CH₃ | 2.36 ppm (s) |
| S—CH₂—CH | 2.85 ppm (dd) |
| C₆H₅—CH₂—CH | 3.00 ppm (dd)<br>3.06 ppm (m) |
| X—CH₃ | 3.89 ppm (s) |
| 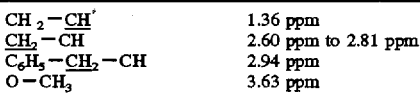 | 4.2 ppm (m) |
| NH—CH | 5.86 ppm (d) |
| Aromatics | 7.2 to 7.3 ppm (m) |

EXAMPLE 2

(+) N-[2-mercapto-1-(phenylmethyl)-ethyl]-N'-methoxy]urea 0.320 ml of hydrazine hydrate were added at 0° C. to a solution of 1.7 g of the compound of Example 1 in 50 ml of tetrahydrofuran, and the mixture was stirred for 90 minutes at 0° C. After evaporating to dryness under reduced pressure, the residue was chromatographed (eluant: methylene chloride—methanol 100-1.5) to obtain 1.05 g of the desired product melting at 70° C. to 72° C.

| Analysis: C₁₁H₁₆N₂O₂S; molecular weight = 240.3 | | | | |
|---|---|---|---|---|
| | % C | % H | % N | % S |
| Calculated: | 54.98 | 6.71 | 11.66 | 13.34 |
| Found: | 54.8 | 6.5 | 11.5 | 13.4 |

NMR Spectrum (CDCl₃)

| | |
|---|---|
| CH₂—CH' | 1.36 ppm |
| CH₂—CH | 2.60 ppm to 2.81 ppm |
| C₆H₅—CH₂—CH | 2.94 ppm |
| O—CH₃ | 3.63 ppm |
| 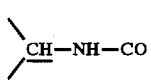CH—NH—CO | 4.24 ppm |
| 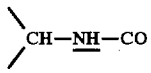CH—NH—CO | 5.86 ppm |
| 7.18 to.7.35 ppm aromatic H's | |

EXAMPLE 3

S-[2-(3-methyl-3-methoxy-ureido)-3-phenyl propyl] ethanethioate

Using the procedure of Example 1, 2.35 g of the isocyanate of preparation 1 and 1.463 ml of N,O-dimethylhyroxylamine hydrochloride and 2.3 ml of triethylamine were reacted to obtain 2.2 g of the desired product melting at 68° C. to 70° C.

NMR Spectrum (CDCl₃) ppm

| | |
|---|---|
| COCH₃ | 2.36 |
| CON—CH₃ | 3.05 |
| CONOCH₃ | 3.55 |
| 4.14 | N—CH—CH₂<br>    |<br>    CH₂ |
| C₆H₅—CH₂—CH<br>and<br>S—CH₂—CH | 2.81–2.97–3.05 |
| NH—CH | 5.92 |
| Aromatics | 7.14 to 7.37 |

EXAMPLE 4

(+) N-[2-mercapto-1-(phenylmethyl)-ethyl]-N'-methoxy-N'-methyl urea

Using the procedure of Example 2, 1.758 g of the product of Example 3 and 0.320 ml of hydrazine hydrate were reacted to obtain after sublimation at 100° C. under reduced pressure, 860 mg of the expected pure product melting at 50° C.

Analysis: C₁₂H₁₈N₂O₂S; molecular weight = 254.4

| | % C | % H | % N | % S |
|---|---|---|---|---|
| Calculated: | 56.67 | 7.13 | 11.01 | 12.61 |
| Found: | 56.7 | 7.1 | 10.8 | 12.5 |

NMR Spectrum CDCl₃ ppm

| | |
|---|---|
| SH—CH₂ | 1.34 |
| SH—CH₂—CH | 2.58 to 2.78 |
| C₆H₅—CH₂—CH | 2.92 |
| C—N—CH₃<br>||<br>O | 3.06 |
| O—CH₃ | 3.58 |
| C₆H₅—CH₂—CH—NH—C—<br>                     ||<br>                     O | 4.17 |
| C—NH—CH<br>||<br>O | 5.94 |
| Aromatics | 7.15 to 7.45 |

EXAMPLE 5

S-[2-(3-methoxy-3-hydroxy-ureido)-3-phenyl-propyl]-ethanethioate

Using the procedure of Example 1, 2.35 g of the isocyanate of Preparation I and 1.225 g of N-methyl hydroxylamine hydrochloride and 2.09 ml of triethylamine were reacted to obtain 1.9 g of the desired product with a Rf=0.36 (eluant: ethyl acetate—n-hexane 7-3).

NMR Spectrum (CDCl₃ ppm

| | |
|---|---|
| N—CH—CH₂<br>    |<br>    CH₂ | 4.1 |
| COCH₃ | 2.34 ppm |
| S—CH₂—CH<br>and<br>C₆H₅—CH₂—CH | 2.3 to 3.1 |
| CONCH₃ | 3.07<br>3.08 |
| NH—CH | 6.11<br>6.18 |
| Aromatics | 7.1 to 7.4 |

EXAMPLE 6

(+) N-hydroxy-N'-[2-mercapto-1-(phenylmethyl)-ethyl]-N-methyl urea

Using the procedure of Example 2, 1.7 g of the product of Example 5 and 0.320 ml of hydrazine hydrate were reacted to obtain 1.2 g of the desired product.

Analysis: C₁₁H₁₆N₂O₂S; molecular weight = 240.3

| | % C | % H | % n | % S |
|---|---|---|---|---|
| Calculated: | 54.98 | 6.71 | 11.66 | 13.34 |
| Found: | 55.2 | 6.8 | 11.6 | 13.4 |

NMR Spectrum CDCl₃) ppm

| | |
|---|---|
| CH₂—SH | 1.35 |
| CH₂—SH | 2.50 to 2.70 |
| C₆H₅—CH₂—CH | 2.75 to 2.95 |
| N—CH₃ | 3.06 |
| CH—NH—CO | 4.12 |
| CH—NH—CO | 6.19 |
| aromatics | 7.15 to 7.35 |
| mobile 1 H | 8.05 |

EXAMPLE 7

(+) S-[[[(2-hydroxy-ethyl)-methyl-amino]-carbonyl]-amino]-3-phenyl propyl]ethanethioate Using the procedure of Example 1, 2.35 g of the isocyanate of Preparation I and 1.1 ml of 2-methylaminoethanol were reacted to obtain after chromatography on silica (eluant: ethyl acetate—n-hexane 9-1), 2 g of the desired product.

IR Spectrum CHCl₃

| | |
|---|---|
| OH | 3620 cm⁻¹ |
| NH | 3425 cm⁻¹ |
| \C=O<br>/ | 1682 cm⁻¹ |
| | O<br>||<br>S—C |
| | 1636 cm⁻¹ |
| | O<br>||<br>NH—C |

| Amide II | 1526 cm⁻¹ |
|---|---|
|  | 1600 cm⁻¹ |
|  | 1496 cm⁻¹ |

EXAMPLE 8

(+) N-(2-hydroxy ethyl)-N'-[2-mercapto-1-(phenylmethyl)-ethyl]-N-methyl urea

Using the procedure of Example 2, 2 g of the product of Example 7 and 0.360 ml of hydrazine hydrate were reacted to obtain after impasting in hexane, 1.2 g of product melting at 86° C., which was crystallized from isopropyl ether to obtain 0.7 g of the desired product melting at 86° C.

Analysis: $C_{13}H_{20}N_2O_2S$; molecular weight = 268.38

|  | % C | % H | % N | % S |
|---|---|---|---|---|
| Calculated: | 58.18 | 7.51 | 10.438 | 11.95 |
| Found: | 58.5 | 7.8 | 10.5 | 11.7 |

IR Spectrum

| OH | 3620 cm⁻¹ |
|---|---|
| NH | 3448 cm⁻¹ |
| C=O | 1636 cm⁻¹ |

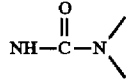

| Amide II | 1518 cm⁻¹ |
|---|---|
| Aromatics | 1497 cm⁻¹ |

EXAMPLE 9

(+) S-[2-[[[bis(2-methoxyethyl)-amino]-carbonyl]-amino]-3-phenyl propyl]ethanethioate Using the procedure of Example 1, 2.35 g of the isocyanate of preparation I and 2 g of di-(methoxymethylamine) were reacted to obtain after chromatography on silica (eluant: methylene chloride—ethyl acetate 7-3), 2 g of the desired product.

IR Spectrum CHCl₃

| =C—NH | 3341 cm⁻¹ |
|---|---|
| C=O | 1689 cm⁻¹ |
|  | 1644 cm⁻¹ |

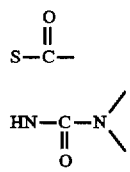

| Amide II | 1535 cm⁻¹ |
|---|---|

EXAMPLE 10

N,N-bis(2-methoxy ethyl)-N'-[2-mercapto-1-(phenylmethyl)-ethyl]urea

Using the procedure of Example 2, 2 g of the product of Example 9 and 0.290 ml of hydrazine hydrate were reacted to obtain after chromatography on silica (eluant: methylene chloride—ethyl acetate 7-3) 1.5 g of the expected product.

Analysis: $C_{16}H_{26}N_2O_3S$; molecular weight = 326.46

|  | % C | % H | % N | % S |
|---|---|---|---|---|
| Calculated: | 58.87 | 8.03 | 8.58 | 9.821 |
| Found: | 58.9 | 8.2 | 8.6 | 9.7 |

IR Spectrum CHCl₃

| SH | 2570 cm⁻¹ |
|---|---|
| =C—NH | 3340 cm⁻¹ |
| C=O | 1642 cm⁻¹ |
| Amide II | 1532 cm⁻¹ |

EXAMPLE 11

Methyl N-[[[2-(acetylthio)-1-(phenylmethyl)-ethyl]-amino]-carbonyl]-glycinate

Using the procedure of Example 1, 2.35 g of the product of Preparation I and 1.9 g of glycine methyl ester hydrochloride and 2.1 ml of triethylamine were reacted to obtain after chromatography on silica (eluant: methylene chloride—ethyl acetate 7-3) and impasting in n-hexane, 2.1 g of the desired product melting at 102° C.

IR Spectrum CHCl₃

| =C—NH | 3425 cm⁻¹ |
|---|---|
|  | 1476 cm⁻¹ |
| CH₃—C | 1440 cm⁻¹ |
| Other C=O | 1684 cm⁻¹ |
| Amide II | 1534 cm⁻¹ |

EXAMPLE 12

(+) N-[[[2-mercapto-1-(phenylmethyl)-ethyl]-amino]-carbonyl]glycine 10 ml of N sodium hydroxide were added at 0° C. to a solution of 1.6 g of the product of Example 11 in 30 ml of methanol and the mixture was stirred for 6 hours at ambient temperature, diluted with water and acidified with N hydrochloric acid. After extraction with methylene chloride, the extracts were washed with water, dried and evaporated to dryness under reduced pressure. After impasting in hexane, 0.65 g of the desired product melting at 110° C. were obtained.

Analysis: $C_{12}H_{16}N_2O_3S$; molecular weight = 268.336

|  | % C | % H | % N | % S |
|---|---|---|---|---|
| Calculated: | 53.713 | 6.01 | 10.439 | 11.949 |
| Found: | 53.8 | 6.1 | 10.3 | 11.9 |

IR Spectrum: Nujol

| Absorption NH/OH | |
|---|---|
| C=O | 1758 cm$^{-1}$ |
|  | 1745 cm$^{-1}$ |
| Aromatic | 1594 cm$^{-1}$ |
| Amide II | 1585 cm$^{-1}$ |
|  | 1510 cm$^{-1}$ |
|  | 1495 cm$^{-1}$ |

EXAMPLE 13

S-(2-ureido-3-phenyl-propyl)-ethanethioate

Using the procedure of Example 1, 3 g of the isocyanate of Preparation 1 and bubbling ammonia through the medium for 45 minutes at 0° C. The medium was diluted with water and extracted with methylene chloride. The extracts were washed, dried and evaporated to dryness under reduced pressure. After chromatography on silica (eluant: ethyl acetate—n-hexane 9-1), 1.6 g of the desired product melting at 90° C. were obtained.

IR Spectrum CHCl$_3$

| Absence of N=C=O | |
|---|---|
| =C—NH$_2$ | 3511 cm$^{-1}$ |
| =C—NH— | 3418 cm$^{-1}$ |
|  | 3384 cm$^{-1}$ |
| C=O | 1681 cm$^{-1}$ |
| NH$_2$ def | 1599 cm$^{-1}$ |
| Amide II | 1525 cm$^{-1}$ |
| Aromatic | 1497 cm$^{-1}$ |

EXAMPLE 14

(+) N-[2-mercapto-1-(phenylmethyl)-ethyl]-urea

Using the procedure of Example 2, 1.2 g of the product of Example 13 and 0.270 ml of hydrazine hydrate were reacted to obtain after crystallization from isopropyl ether, 0.65 g of the desired product melting at 118° C.

| Analysis: C$_{10}$H$_{14}$N$_2$OS; molecular weight = 210.3 | | | | |
|---|---|---|---|---|
|  | % C | % H | % N | % S |
| Calculated: | 57.114 | 6.71 | 13.32 | 15.246 |
| Found: | 56.9 | 6.7 | 13.0 | 15.1 |

IR Spectrum

| NH/NH$_2$ | 3515 cm$^{-1}$ |
|---|---|
|  | 3419 cm$^{-1}$ |
| C=O complex | 1679 cm$^{-1}$ |
| NH$_2$ def | 1597 cm$^{-1}$ |
| Amide II | 1518 cm$^{-1}$ |
| Aromatic | 1497 cm$^{-1}$ |
| SH | 2575 cm$^{-1}$ |

EXAMPLE 15

S-[2-(3-phenyl-ureido)-3-phenyl propyl] ethanethioate

Using the procedure of Example 1, 3 g of the isocyanate of Preparation 1 and 1.39 ml of aniline were reacted to obtain after chromatography on silica (eluant: ethyl acetate—n-hexane 5-5), 3 g of the desired product.

IR Spectrum CHCl$_3$

| Absence of N=C=O | |
|---|---|
| CNH | 3427 cm$^{-1}$ |
|  | 3367 cm$^{-1}$ |
| C=O | 1682 cm$^{-1}$ |
| Complex |  |
| Amide II | 1544 cm$^{-1}$ |
|  | 1527 cm$^{-1}$ |
| Aromatic | 1599 cm$^{-1}$ |
|  | 1499 cm$^{-1}$ |

EXAMPLE 16

(+) N-[2-mercapto-1-(phenylmethyl)-ethyl]-N']-phenyl urea

Using the procedure of Example 2, 2 g of the product of Example 15 and 0.330 ml of hydrazine hydrate were reacted to obtain after chromatography on silica (eluant: ethyl acetate—n-hexane 6-4) 1.1.g of product which was impasted in hexane, then crystallized from a mixture of isopropyl ether and ethyl acetate (1-1) to obtain 0.82 g of the desired product melting at 138° C.

| Analysis: C$_{16}$H$_{18}$N$_2$OS; molecular weight = 286.398 | | | | |
|---|---|---|---|---|
|  | % C | % H | % N | % S |
| Calculated: | 67.101 | 6.33 | 9.78 | 11.195 |
| Found: | 66.9 | 6.3 | 9.6 | 11.2 |

NMR Spectrum CDCl$_3$) (250 MHz) ppm

| SH—CH$_2$ | 1.33 |
|---|---|
| HS—CH$_2$ | 2.67 |
| C$_6$H$_5$—CH$_2$—CH | 2.88 |
| CH$_2$—CH—N—CO<br>\|<br>CH$_2$ | 4.25 |
| Aromatics | 7.05 to 7.30 |

EXAMPLE 17

S-[2-[3-bis(propyl)-ureido]-3-phenyl-propyl]-ethanethioate

Using the procedure of Example 1, 3 g of the isocyanate of Preparation 1 and 1.94 ml of dipropylamine were reacted to obtain 3 g of the desired product melting at 60° C.

EXAMPLE 18

(+) N,N-dipropyl-N'-[2-mercapto-1-(phenyl methyl)-ethyl]urea

Using the procedure of Example 2, 1.5 g of the product of Example 17 were reacted to obtain 680 mg of the desired product melting at 68° C.

EXAMPLE 19

S-[2-[3,3-bis(2-hydroxy-ethyl)-ureido]-3-phenyl-propyl]ethanethioate

Using the procedure of Example 1, 2.35 g of the isocyanate of Preparation 1 and 1.25 ml of diethanolamine were reacted to obtain after chromatography on silica (eluant: methylene chloride—methanol (95-5)) 2.5 g of the desired product.

IR Spectrum (CHCl$_3$)

| | |
|---|---|
| OH | 3620 cm$^{-1}$ |
| NH | 3348 cm$^{-1}$ |
| C=O | 1687 cm$^{-1}$ |
| | 1627 cm$^{-1}$ |
| Amide II | 1531 cm$^{-1}$ |
| Aromatic | 1497 cm$^{-1}$ |

EXAMPLE 20

(+) N,N-bis(2-hydroxy ethyl)-N'-[2-mercapto-1-(phenylmethyl)ethyl]-urea

Using the procedure of Example 2, 2 g of the product of Example 19 and 0.358 ml of hydrazine hydrate were reacted to obtain after chromatography on silica (eluant: methylene chloride—methanol 9-1), 0.95 g of the desired product.

Analysis: C$_{14}$H$_{22}$N$_2$O$_3$S; molecular weight = 298.41

| | % C | % H | % N | % S |
|---|---|---|---|---|
| Calculated: | 56.35 | 7.43 | 9.38 | 10.745 |
| Found: | 56.2 | 7.7 | 9.2 | 10.7 |

NMR Spectrum CDCl$_3$ (250 MHz) ppm

| | |
|---|---|
| SH—CH$_2$ | 1.38 |
| HS—CH$_2$CH | 2.66 |
| C$_6$H$_5$CH$_2$CH | 2.89 |
| NCH$_2$CH$_2$O | 3.37 |
| | 3.72 |
| Proton | 3.82 |
| CH$_2$—CHNCO<br>\|<br>CH$_2$ | 4.13 |
| NH—CH | 6.04 |
| Aromatics | 7.2 to 7.4 |

EXAMPLE 21

S-[2-[[(1-pyrrolidinyl)-carbonyl]-amino]-3-phenyl propyl]ethanethioate

Using the procedure of Example 1, 2.35 g of the product of Preparation 1 and 1.25 ml of pyrrolidine were reacted to obtain 1.8 g of the desired product melting at 100° C. to 102° C.

NMR Spectrum CDCl$_3$

| | |
|---|---|
| S—Ac | 2.35 ppm |
| the CH$_2$'s in beta position of N | 1.38 ppm |
| the CH$_2$'s in alpha position of N | 3.26 ppm |
| C$_6$H$_5$CH$_2$ and CH$_2$—S | 2.6 to 3.1 ppm |
| CH—NH | 4.16 ppm |
| NH | 4.56 ppm |
| aromatic H | 7.2 to 7.3 ppm |

EXAMPLE 22

(+) N-[2-mercapto-1-(phenylmethyl)-ethyl]-1-pyrrolidine carboxamide

Using the procedure of Example 2, 1.7 g of the product of Example 21 and 0.290 ml of hydrazine hydrate were reacted to obtain 860 mg of the desired product melting at 92° C. to 94° C.

Analysis: C$_{14}$H$_{20}$N$_2$OS; molecular weight = 264.4

| | % C | % H | % N | % S |
|---|---|---|---|---|
| Calculated: | 63.6 | 7.6 | 10.6 | 12.13 |
| Found: | 63.4 | 7.7 | 10.3 | 12.0 |

NMR Spectrum (CDCl$_3$) ppm

| | |
|---|---|
| CH$_2$—SH | 1.31 |
| CH$_2$ in position 3 and 4 | 1.89 |
| CH$_2$ in position 2 and 5 | 3.30 |
| CH$_2$—SH | 2.67 |
| C$_6$H$_5$—CH$_2$ | 2.91 |
| CH$_2$—CH—CH$_2$<br>\|<br>NH—CO | 4.24 |
| NH—CO | 4.40 |
| Aromatics | 7.15 to 7.35 |

EXAMPLE 23

S-[2-[[hexahydro-1H-1-azepinyl)-carbonyl]-amino]-3-phenyl propyl]ethanethioate

Using the procedure of Example 1, 2.35 g f the isocyanate of Preparation 1 and 2.52 ml of hexamethyleneimine were reacted to obtain after chromatography on silica.(eluant: methylene chloride—ethyl acetate 7-3) and impasting in hexane, 2.5 g of the desired product melting at 97° C.

IR Spectrum

| | |
|---|---|
| O<br>\|\|<br>S—C—Me | 1681 cm$^{-1}$ |
| =C—NH | 3435 cm$^{-1}$ |
| C=O | 1634 cm$^{-1}$ |

EXAMPLE 24

(+) hexahydro-N-[2-mercapto-1-(phenyl-methyl)-ethyl]-1H-azepine-1-carboxamide

Using the procedure of Example 2, 1.5 g of the product of Example 23 and 0.260 ml of hydrazine hydrate were reacted to obtain after crystallization from isopropyl ether 0.7 g of the desired product melting at 102° C.

Analysis: C$_{16}$H$_{24}$N$_2$OS; molecular weight = 292.446

| | % C | % H | % N | % S |
|---|---|---|---|---|
| Calculated: | 65.713 | 8.27 | 9.58 | 10.964 |
| Found: | 65.9 | 8.4 | 9.5 | 11.1 |

IR Spectrum (CHCl$_3$)

| | |
|---|---|
| C=O | 1633 cm$^{-1}$ |
| Amide II | 1589 cm$^{-1}$ |
| =C—NH | 3344 cm$^{-1}$ |

EXAMPLE 25

S-[2-[[(1-piperidinyl)-carbonyl]-amino]-3-phenylpropyl]ethanethioate

Using the procedure of Example 1, 1.81 g of the isocyanate of Preparation 1 and 1.74 ml of pyridine were reacted to obtain 1.775 g of the desired product melting at 114° C. to 116° C.

NMR Spectrum (CDCl$_3$) ppm

| | |
|---|---|
| S—COCH$_3$ | 2.35 |
| CH$_2$—N—CO | 3.25 |
| cyclic CH$_2$'s | 1.51 |
| C$_6$H$_5$—CH$_2$ and CH$_2$S | 2.74 |
|  | 2.91 to 3.20 |
| NH—CH< | 4.15 |
| NH—CH< | 4.83 |
| Aromatics | 7.15 to 7.35 |

EXAMPLE 26

(+) N-[2-mercapto-1-(phenylmethyl)-ethyl]-1-pyridine carboxamide

Using the procedure of Example 2, 1.6 g of the product of Example 25 and 0.290 ml of hydrazine hydrate were reacted to obtain after chromatography on silica (eluant: methylene chloride—ethyl acetate 85-15) 900 mg of the desired product melting at 115° C. to 117° C. after impasting in ether.

Analysis: C$_{14}$H$_{22}$N$_2$OS; molecular weight = 278.4

| | % C | % H | % N | % S |
|---|---|---|---|---|
| Calculated: | 64.71 | 7.96 | 10.06 | 11.52 |
| Found: | 64.7 | 8.1 | 10.0 | 11.4 |

NMR Spectrum (CDCl$_3$)

| | |
|---|---|
| SH—CH$_2$ CH$_2$ in position 3, 4 and 5 (piperidine) | 1.53 |
| C$_6$H$_5$—CH$_2$— CH—CH$_2$ | 2.87 to 3.00 |
| CH$_2$ in position 2 and 6 | 3.28 |
| CH—NH—CO | 4.23 |
| CH—NH—CO | 4.64 |
| Aromatics | 7.20 to 7.33 |

EXAMPLE 27

S-[2-[[(4-thiomorpholinyl)-carbonyl]-amino]-3-phenyl ethyl]ethanethioate

Using the procedure of Example 1, 1.8 g of the isocyanate of Preparation 1 and 1.76 ml of thiomorpholine were reacted to obtain 2 g of the desired product.

NMR Spectrum

| | |
|---|---|
| S—AC the cyclic CH$_2$—S's | 2.36 ppm<br>2.53 ppm |
| the CH$_2$—N—C's<br>‖<br>O | 3.61 ppm |
| C$_6$H$_5$—CH$_2$ and CH$_2$—S—AC | 2.75 ppm 1 H<br>2.91 to 3.11 pm 3 H |
| NH—CH< | 4.15 ppm |
| NH—CH | 4.93 ppm |
| Phenyl | 7.20 to 7.34 ppm |

EXAMPLE 28

(+) N-[2-mercapto-1-(phenylmethyl)-ethyl]-4-thiomorpholinecarboxamide

Using the procedure of Example 2, 1.6 g of the product of Example 27 and 0.290 ml of hyrazine hydrate were reacted to obtain 1.15 g of the desired product melting at 98° C. to 100° C.

Analysis: C$_{14}$H$_{20}$N$_2$OS; molecular weight = 296.5

| | % C | % H | % N | % S |
|---|---|---|---|---|
| Calculated: | 56.72 | 6.80 | 9.45 | 21.63 |
| Found: | 57.0 | 6.9 | 9.4 | 21.5 |

NMR Spectrum (CDCl$_3$) ppm

| | |
|---|---|
| SH CH$_2$ | 1.31 |
| C$_6$H$_5$—CH$_2$CH<br>\|<br>CH$_2$ | 2.53 |
| CH$_2$—CH$_2$—S—CH$_2$—CH$_2$ | 2.69–2.9 |
| CH$_2$—CH$_2$—N—CH$_2$—CH$_2$ | 3.63 |
| CH$_2$—CH—CH$_2$<br>\|<br>NH—CO | 4.24 |
| CH$_2$—CH—CH$_2$<br>NH—CO<br>Aromatics | 4.6<br>7.19 to 7.35 |

EXAMPLE 29

S-[2-[[(4-morpholinyl)-carbonyl]-amino]-3-phenyl propyl]ethanethioate

Using the procedure of Example 1, 2.2 g of the isocyanate of Preparation 1 and 1.8 ml of morpholine were reacted to obtain after chromatography on silica (eluant: methylene chloride—methanol 100-1), 1.9 g of the desired product melting at 105° C.

IR Spectrum (CHCl₃)

| NH complex | 3428 cm⁻¹ |
|---|---|
| C=O | 1675 |
|  | 1645 |
| Aromatic | 1603 |
| + | 1580 |
| Amide II | 1522 |
|  | 1497 |

EXAMPLE 30

(+) N-[2-mercapto-1-(phenylmethyl)-ethyl]-4-morpholine carboxamide

Using the procedure of Example 2, 1.9 g of the product of Example 29 and 0.34 ml of hydrazine hydrate were reacted to obtain after chromatography on silica (eluant: methylene chloride—methanol 100-1.5), 1.5 g of the desired product melting at 84° C.

IR Spectrum (CHCl₃)

| SH | 2575 cm⁻¹ |
|---|---|
| =C—NH | 3457 cm⁻¹ |
| C=O | 1644 cm⁻¹ |
| Amide II | 1509 cm⁻¹ |

EXAMPLE 31

S-[2-[[(4-(cis-2,6-dimethyl)-morpholinyl]-carbonyl]-amino]-3-phenyl propyl]-ethanethioate Using the procedure of Example 1, 4.7 g of the isocyanate of Preparation 1 and 3.7 ml of 2,6-dimethylmorpholine were reacted to obtain 1.2 g of product (isomer A) isolated from ether and melting at 120° C. to 122° C. After chromatographing of the mother liquors (eluant: ethyl acetate—hexane (7-3)), another 2.5 g of isomer A melting at 120° C. to 122° C., and 1 g of product (isomer B) melting at 98° C. to 100° C. were obtained.

NFFR Spectrum—isomer A (CDCl₃ 250 MHz)

| $\underline{CH_3}$—CH | 1.18 ppm (d, J=6 Hz) |
|---|---|
| S—CO—$\underline{CH_3}$ | 2.35 ppm (s) |
| NH—CH | 4.91 ppm (d) |
| CO—N$\underline{CH}$—CH₂<br>$\vert$<br>CH₂ | 4.17 ppm (m) |
| 3.4 to 3.7 (m) | 4 H |
| 2.88 to 3.13 (m) | 3 H other protons |
| 2.73 (dd) | 1 H non aromatics |
| 2.45 (m) | 2 H |
| 7.15 to 7.35 (m) | aromatics |

EXAMPLE 32

(+) cis-2,6-dimethyl-N-[2-mercapto-1-(phenylmethyl)-ethyl]-4-morpholine carboxamide (isomer A)

Using the procedure of Example 2, 2.1 g of the product, isomer A, of Example 31 and 0.320 ml of hydrazine hydrate were reacted to obtain 1.3 g of the desired product melting at 120° C. to 122° C.

Analysis: C₁₆H₂₄N₂O₂S; molecular weight = 308.45

|  | % C | % H | % N | % S |
|---|---|---|---|---|
| Calculated: | 62.31 | 7.84 | 9.08 | 10.4 |
| Found: | 62.3 | 8.0 | 9.0 | 10.5 |

NMR Spectrum (CDCl₃) ppm

| the $\underline{CH_3}$—CH's | 1.18–1.19 |
|---|---|
| $\underline{SH}$—CH₂ | 1.31 |
| C₆H₅$\underline{CH_2}$—CH—$\underline{CH_2}$—S | 4.49 |
| and | 2.68 |
| N—$\underline{CH_2}$—CH | 2.91 |
| and | 3.65 |
| O—$\underline{CH}$—CH₂<br>$\vert$<br>CH₃ | 3.52 |
| N—$\underline{CH}$—CH₂<br>$\vert$<br>CH₂ | 4.25 |

EXAMPLE 33

(+) S-[2-[[(4-methyl-1-piperazinyl)-carbonyl]-amino]-3-phenyl propyl]ethanethioate Using the procedure of Example 1, 2.35 g of the isocyanate of Preparation 1 and 1.44 ml of N-methyl piperazine were reacted to obtain after chromatography on silica, (eluant: methylene chloride—methanol (9-1), 3.2 g of the desired product melting at 78° C.

IR Spectrum (CHCl₃)

| NH | 3430 cm⁻¹ |
|---|---|
| C=O | 1676 cm⁻¹ |
|  | 1639 cm⁻¹ |
| Amide II | 1520 cm⁻¹ |

EXAMPLE 34

(+) 4-methyl-N-[2-mercapto-1-(phenylmethyl)-ethyl]-1-piperazinecarboxamide hydrochloride Using the procedure of Example 1, 2 g of the product of Example 33 and 0.36 ml of hydrazine hydrate were reacted to obtain after chromatography on silica (eluant: methylene chloride—methanol 9-1), 1.2 g of product in the form of the base. To obtain the hydrochloride, 1.2 g of the base were dissolved in 10 ml of ethyl acetate and a saturated ethanolic solution of hydrochloric acid was added until a pH of 1 was obtained to recover 1 g of the desired hydrochloride melting at 170° C. After crystallization from an ethyl acetate—isopropanol mixture, 0.75 g of the product melted at 176° C.

Analysis: C₁₅H₂₄ClN₃OS; molecular weight = 329.895

|  | % C | % H | % N | % Cl | % S |
|---|---|---|---|---|---|
| Calculated: | 54.61 | 7.33 | 12.74 | 10.746 | 9.72 |
| Found: | 54.5 | 7.5 | 12.6 | 11.0 | 9.6 |

IR Spectrum (CHCl₃)

| | |
|---|---|
| NH | 3430 cm⁻¹ |
| \C=O / | 1676 cm⁻¹ 1639 cm⁻¹ |
| Amide II | 1520 cm⁻¹ |

EXAMPLE 35

(+) S-[2-[[(4-phenyl)-1-piperazinyl)-carbonyl]-amino]-3-phenyl propyl]ethanethioate Using the procedure of Example 1, 2.35 g of the isocyanate of Preparation 1 and 2 ml of 1-phenyl piperazine were reacted to obtain after chromatography on silica (eluant: methylene chloride—ethyl acetate 9-1), 2.94 g of the desired product melting at 100° C.

IR Spectrum (CHCl₃)

| | |
|---|---|
| NH | 3430 cm⁻¹ |
| C=O | 1674 cm⁻¹ |
| | 1642 cm⁻¹ |
| Aromatic | 1600 cm⁻¹ |
| | 1581 cm⁻¹ |
| | 1495 cm⁻¹ |

EXAMPLE 36

(+) N-(2-mercapto-1-(phenylmethyl)-ethyl]-4-phenyl-1-piperazine carboxamide

Using the procedure of Example 2, 1.5 g of of the product of Example 35 and 0.22 ml of hydrazine hydrate were reacted to obtain after chromatography on silica (eluant: methylene chloride—ethyl acetate 9-1), 0.7 g of the expected-product melting at 122° C. after impasting in heptane.

Analysis: C₂₀H₂₅N₃OS; molecular weight = 355.5

| | % C | % H | % N | % S |
|---|---|---|---|---|
| Calculated: | 67.572 | 7.088 | 11.82 | 9.019 |
| Found: | 67.9 | 7.2 | 11.9 | 8.9 |

NMR Spectrum (CDCl₃) ppm

| | |
|---|---|
| SH—CH₂ | 1.32 |
| \SHCH₂CH / | 2.6  1 |
| C₆H₅—CH₂—CH | at 3.0 |
| —N⌒N— ⌣ | 3.16 3.50 |

-continued

| | |
|---|---|
| CH₂—CH—NCO \| CH₂ | 4.27 |
| NH—CH | 4.72 |
| Aromatics | 6.93 |
| | 7.2 to 7.35 |

EXAMPLE 37

(+) S-[2-[[[4-[3-(trifluoromethyl)-phenyl]-1-piperazinyl]carbonyl]-amino]-3-phenyl propyl] ethanethioate Using the procedure of Example 1, 2.35 g of the isocyanate of Preparation 1 and 2.81 ml of 4-[3-(trifluoromethyl)-phenyl]-piperazine were reacted to obtain 3.9 g of the desired product melting at 78° C. to 80° C. after crystallization from hexane.

NMR Spectrum (CDCl₃) ppm

| | |
|---|---|
| S—Ac | 2.37 (s) |
| —N⌒N— ⌣ | 3.20 (m) 4 H 3.49 (m) 4 H |
| C₆H₅—CH₂ and S—CH₂ | 2.70 to 3.2 (m) |
| CH₂—CH—CH₂ \| NH—CO | 4.17 (m) 5.06 (d) |
| Aromatics | 7.03 to 7.40 (m) 4 H |

EXAMPLE 38

(+) N-[2-mercapto-1-(phenylmethyl)-ethyl]-4-[3-trifluoromethyl)-phenyl]-1-piperazine carboxamide Using the procedure of Example 2, 2.3 g of the product of Example 37 and 0.266 ml of hydrazine hydrate were reacted to obtain 1.4 g of the desired product melting at 130° C. to 132° C.

Analysis: C₂₁H₂₄F₃N₃OS; molecular weight = 423.5

| | % C | % H | % N | % S | % F |
|---|---|---|---|---|---|
| Calculated: | 59.56 | 5.71 | 9.92 | 7.57 | 13.46 |
| Found: | 59.6 | 5.8 | 9.9 | 7.6 | 13.6 |

NMR Spectrum (CDCl₃) ppm

| | |
|---|---|
| SH | 1.33 |
| SH—CH₂ | 2.6 to 2.80 |
| C₆H₅—CH₂ | 2.80 to 3.05 |
| —N⌒N— ⌣ | 3.20 3.51 |

| | |
|---|---|
| —CH— <br> \| <br> NH—CO | 4.25 |
| \| <br> —CH—NH—CO <br> \| | 4.72 |

EXAMPLE 39

(+S-[2-[[[4-(4-chlorophenyl)-1-piperazinyl]-carbonyl]-amino]-3-phenyl propyl]ethanethioate Using the procedure of Example 1, 2.35 g of the isocyanate of Preparation 1 and 2.55 g of p-chlorophenyl piperazine were reacted to obtain 2.8 g (after impasting in hexane) of the desired product. After chromatography on silica (eluant: ethyl acetate—hexane 7-3) 2.5 g of the expected product melted at 140° C.

IR Spectrum CHCl$_3$

| | |
|---|---|
| =C—NH | 3430 cm$^{-1}$ |
| C=O | 1676 cm$^{-1}$ |
| | 1644 cm$^{-1}$ |
| Aromatic | 1598-1572-1496 cm$^{-1}$ |
| Amide II | 1522 cm$^{-1}$ |

EXAMPLE 40

(+) 4-(4-chlorophenyl)-N-[2-mercapto-1-(phenylmethyl)-ethyl]-1- piperazine carboxamide Using the procedure of Example 2, 2.5 g of the product of Example 39 and 0.340 ml of hydrazine hydrate were reacted to obtain 1.8 g of the desired product which after crystallization from hexane melted at 140° C. After chromatography on silica (eluant: ethyl acetate—hexane 1-1), 0.8 g of the expected product melting at 148° C. were obtained.

Analysis: C$_{20}$H$_{24}$N$_3$ClOS; molecular weight = 389.951

| | % C | % H | % N | % Cl | % S |
|---|---|---|---|---|---|
| Calculated: | 61.6 | 6.2 | 10.77 | 9.091 | 8.22 |
| Found: | 61.5 | 6.1 | 10.7 | 9.3 | 8.3 |

IR Spectrum

| | |
|---|---|
| SH | 2580 cm$^{-1}$ |
| =C—NH | 3450 cm$^{-1}$ |
| C=O | 1645 cm$^{-1}$ |
| Aromatic <br> + <br> Amide II | 1598-1509-1497 cm$^{-1}$ |

Operating as in Examples 1 and 2 respectively, the isocyanate obtained in Step F of the preparation, and the appropriate reagents were reacted to obtain the products of Examples 41 to 58.

EXAMPLE 41: S-[2-(3,3-dimethyl-ureido)-3-phenylpropyl]ethanethioate melting at 70° C.

EXAMPLE 42: (+) N,N-dimethyl-N'[1-(mercaptomethyl)-2-phenylethyl]urea melting at 60° C.

EXAMPLE 43: S-[2-[3-(2-phenylethyl)-ureido]-3-phenylpropyl]ethanethioate.

EXAMPLE 44: (±) N-[1-(mercaptomethyl)-2-phenylethyl]-N'-(2-phenylethyl) urea melting at approx. 62° C.

EXAMPLE 45: S-[2-(3-methyl-ureido)-3-phenyl-propyl]ethanethioate melting at 80° C.

EXAMPLE 46: (±) N-[1-(mercaptomethyl)-2-phenylethyl]-N'-methyl) urea melting at 66° C.

EXAMPLE 47: S-[2-[[(4-hyroxyethyl-1-piperazinyl)-carbonyl]amino]-3-phenylpropyl] ethanethioate.

EXAMPLE 48: (±) 4-(2-hydroxyethyl)-N-[1-(mercaptomethyl)-2-phenylethyl]-1-piperazine carboxamide and its hydrochloride.

The hydrochloride was obtained as in Example 34 and melted at 210° C.

EXAMPLE 49: S-[2-[[(4-ethyl-1-piperazinyl)-carbonyl]-amino]-3-phenylpropyl]ethanethioate.

EXAMPLE 50: (±) 4-ethyl-N-[1-(mercaptomethyl)-2-phenylethyl]-1-piperazine carboxamide and its hydrochloride.

The hyrochloride was obtained as in Example 34 and melted at 198° C.

EXAMPLE 51: S-[2-[[(4-phenylmethyl-1-piperazinyl)-carbonyl]-amino]-3-phenylpropyl] ethanethioate.

EXAMPLE 52: (±) N-[-1-(mercaptomethyl)-2-phenylethyl-4-(phenylethyl)-1-piperazine carboxamide and its oxalate.

The oxalate was prepared from the base dissolved in ethyl acetate by addition of an oxalic acid solution in an ethyl acetate—methanol mixture and the product melted at 192° C.

EXAMPLE 53: (±) S-[2-[[(2-benzoylhydrazo)-carbonyl]-amino]-3-phenylpropyl]ethanethioate melting at 122° C.

EXAMPLE 54: (±) 2-benzoylhydrazide of [1-(mercaptomethyl)-2-phenylethyl]carbamic acid melting at 158° C.

EXAMPLE 55: (±) S-[2-[[[(2,3-dihydro-2-oxo-5-phenyl-1H-1,4-benzodiazepin-3-yl)-amino]-carbonyl]amino]-3-phenylpropyl]ethanethioate melting at 210° C.

EXAMPLE 56: N-(2,3-dihydro-1-methyl-2-oxo-5-phenyl-1H-1,4-benzodiazepin-3-yl)-N'-[1-(mercaptomethyl)-2-phenylethyl]urea melting at 235° C.

EXAMPLE 57: (±) N-[[[1-[(acetylthio)-methyl]-2-phenylethyl]amino]-carbonyl]-glycine melting at 120° C.

EXAMPLE 58: S-[2-[-(4-propyl-1-piperazinyl)-carbonyl]-amino]-3-phenylpropyl]ethanethioate.

EXAMPLE 59: (±) N-[1-(mercaptomethyl)-2-phenylethyl]-4-propyl-1-piperazine carboxamide and its hydrochloride.

2.5 g of the product of Example 58 in 20 ml of ethanol and 4 ml of an ethanolic solution of (6.6N) hydrochloric acid were stirred for 24 hours at ambient temperature. The solvent was evaporated off and the residue was taken up in ethyl acetate, left to crystallize and separated. The residue was taken up in hot isopropanol, chilled, separated and dried at 60° C. under reduced pressure to obtain 1.2 g of the expected product in the form of the hydrochloride melting at 192° C.

Using the procedure of Examples 1 to 58 respectively, the isocyanate of Step F of the preparation and the appropriate reagents were reacted to obtain the products of Examples 60 to 79.

EXAMPLE 60: (±) S-[2-[[[4-(3-phenyl-2-propenyl)-1-piperazinyl]carbonyl]-amino]-3-phenylpropyl] ethanethioate.

EXAMPLE 61: (±) N-[1-(mercaptomethyl)-2-phenylethyl]-4-(3-phenyl-2-propenyl)-1-piperazine carboxamide and its hydrochloride melting at 211° C.

EXAMPLE 62: S-[2-[[(hexahydro-1H-1,4-diazepin-1-yl)-carbonyl]amino]-3-phenylpropyl] ethanethioate.

EXAMPLE 63: (±) hexahydro N-[1-(mercaptomethyl)-2-phenyl-ethyl]-1H-1,4-diazepin-1-carboxamide and its hydrochloride melting at 165° C.

EXAMPLE 64: S-[2-[[[4-(2-propenyl)-1-piperazinyl]-carbonyl]-amino]-3-phenylpropyl] ethanethioate melting at 80° C.

EXAMPLE 65: (±) N-[1-(mercaptomethyl)-2-phenylethyl]-4-(2-propenyl)-1-piperazine carboxamide and its hyrochloride melting at 190° C.

EXAMPLE 66: S-[2-[[[4-(1-methylethyl)-1-piperazinyl]-carbonyl]-amino]-3-phenylpropyl] ethanethioate.

EXAMPLE 67: (±) N-[1-(mercaptomethyl)-2-phenylethyl]-4-(1-methylethyl)-1-piperazine carboxamide and its hydrochloride melting at 202° C.

EXAMPLE 68: (±) S-[2-[[[4-(2-propynyl)-1-piperazinyl]-carbonyl]-amino]-3-phenylpropyl] ethanethioate.

EXAMPLE 69: (±) N-[1-(mercaptomethyl)-2-phenylethyl]-4-(2-propynyl)-1-piperazine carboxamide and its hydrochloride melting at 170° C.

EXAMPLE 70: Ethyl (±) 4-[[[1-[(acetylthio)-methyl]-2-phenylethyl]-amino]-carbonyl]-1-piperazine carboxylate melting at 84° C.

EXAMPLE 71: Ethyl (±) 4-[[[1-(mercaptomethyl)-2-phenylethyl]-amino]-carbonyl]-piperazine-1-carboxylate.

The base was obtained by the addition of a saturated aqueous solution of sodium bicarbonate to the oily residue of the hydrochloride and melted at 121° C.

EXAMPLE 72: Ethyl (±) 4-[[[1-[(acetylthio)-methyl]-2-phenylethyl]-amino]-carbonyl]-1-piperazine acetate.

EXAMPLE 73: Ethyl (±) 4-[[[1-(mercaptomethyl)-2-phenylethyl]-amino]-carbonyl]-1-piperazine acetate and its oxalate.

The oxalate was prepared from the base as in Example 52. The base was obtained by the addition of potassium carbonate to the oily residue containing the hydrochloride.

EXAMPLE 74: S-[2-[[[4-(2-phenylethyl)-1-piperazinyl]-carbonyl]amino]-3-phenylpropyl] ethanethioate melting at 100° C.

EXAMPLE 75: (±) N-[1-(mercaptomethyl)-2-phenylethyl]-4-(2-phenylethyl)-1-piperazine carboxamide and its hydrochloride melting at 215° C.

EXAMPLE 76: (±) S-[2-[[[[1-(phenylmethyl)-4-piperidinyl]-amino]carbonyl]-amino]-3-phenylpropyl]-ethanethioate.

EXAMPLE 77: (±) N-[1-(mercaptomethyl)-2-phenylethyl]-N'-[1-(phenylmethyl)-4-piperidinyl]-urea and its hydrochloride melting at 212° C.

EXAMPLE 78: (±) S-[2-[[[2-(dimethylamino)-ethyl]-amino]-carbonyl]amino]-3-phenylpropyl] ethanethioate melting at 52° C. to 54° C.

EXAMPLE 79: (±) N-[2-(diethylamino)-ethyl]-N'-[1-(mercaptomethyl)-2-phenylethyl]urea.

The base was obtained by the addition of a saturated aqueous solution of sodium bicarbonate to the oily residue of the hydrochloride.

In Examples 80 to 93, the starting product was identical to that of Step E of the preparation. The synthesis of the isocyanate, identical to that indicated in Step F, is carried out in situ.

EXAMPLE 80: Phenylmethyl (±) N-[[[1-[(acetylthio)-methyl]-2-phenylethyl]-amino]-carbonyl]glycinate melting at 80° C. to 82° C.

EXAMPLE 81: Phenylmethyl (±) N-[[[1-(mercaptomethyl)-2-phenylethyl]-amino]-carbonyl] glycinate melting at 116° C. to 118° C.

The elimination of the acyl group was carried out using hydrazine hydrate.

EXAMPLE 82: Methyl (±) 3-[[[[1-[(acetylthio)-methyl]-2-phenylethyl]-amino]-carbonyl]-amino]-propanoate melting at 60° C. to 62° C.

EXAMPLE 83: (±) 3-[[[[(1-mercaptomethyl)-2-phenylethyl]-amino]carbonyl]-amino]propanoic acid.

1.89 g of the product of Example 81 in 18 ml of methanol were cooled down to 0° C. and 11.2 ml of N sodium hydroxide were added. The mixture was stirred for 16 hours at ambient temperature and 5.6 ml of N sodium hydroxide were added. The mixture was stirred for 1 hour and the solvent was evaporated off under reduced pressure. The reaction medium was poured into 25 ml of 2N hydrochloric acid which contained 25 ml of water. Extraction took place with ethyl acetate and after concentration to dryness under reduced pressure, the residue was taken up in methylene chloride and concentrated to dryness again. The residue was crystallized from ether and after crystallization from ethyl acetate acidified with 2N hydrochloric acid, 0.74 g of the expected product melting at 88° C. to 90° C. were obtained.

EXAMPLE 84: (±) 3-[[[[1-[(acetylthio)-methyl]-2-phenylethyl]amino]-carbonyl]-amino]benzoic acid melting at 198° C. to 200° C.

EXAMPLE 85: (±) 3-[[[[(1-mercaptomethyl)-2-phenylethyl]-amino]-carbonyl]-amino]-benzoic acid melting at 178° C. to 180° C.

The elimination of the acyl group was carried out as in Example 83.

EXAMPLE 86: (±) 2-[[[[(1-[(acetylthio)-methyl]-2-phenyl-ethyl]amino]-carbonyl]-amino]benzoic acid melting at 178° C. to 180° C.

EXAMPLE 87: (±) 2-[[[[(1-mercaptomethyl)-2-phenylethyl]-amino]-carbonyl]-amino]benzoic acid melting at 162° C. to 164° C.

The elimination of the acyl group was carried out as in Example 83.

EXAMPLE 88: (±) 4-[[[[(1-[(acetylthio)-methyl]-2-phenylethyl]amino]-carbonyl]-amino]benzoic acid melting at 218° C. to 220° C.

EXAMPLE 89: (!) 4-[[[[(1-mercaptomethyl)-2-phenylethyl]-amino]carbonyl]-amino benzoic acid melting at 160° C. to 162° C.

The elimination of the acyl group was carried out as in Example 83.

EXAMPLE 90: (±) S-[2-[[[[2-(4-moropholinyl)-ethyl]-amino]-arbonyl]-3-phenylpropyl] ethanethioate melting at 78° C. to 80° C.

EXAMPLE 91: (±) N-[1-(mercaptomethyl)-2-phenylethyl]-N'-[2-(4-morpholinyl)-ethyl]urea melting at 88° C. to 90° C.

The elimination of the acyl group was carried out as in Example 58 and the base was obtained as in Example 71.

EXAMPLE 92: (±) S-[2-[[(1-piperazinyl)-carbonyl]-amino]-3-phenyl propyl]ethanethioate.

EXAMPLE 93: (±) N-[1-(mercaptomethyl)-2-phenylethyl]-1-piperazinecarboxamide in the form of the hydrochloride melting at 238° C. to 240° C.

EXAMPLE 94: Methyl (±) N-3-[[[(1-(mercaptomethyl)-2-phenethyl]amino]-carbonyl] glycinate.

2.04 g of the product of Example 11 in 5 ml of methanol in the presence of 20 ml of a methanolic solution of hydrochloric acid were stirred for 16 hours at ambient temperature. After concentrating, the oil was taken up in methylene chloride, washed with water, dried and the solvent was eliminated under reduced pressure. The residue was taken up in a hexane—ether mixture, separated, and dried under reduced pressure at ambient temperature to obtain 1.442 g of expected product melting at 70° C. to 72° C.

EXAMPLE 95: Methyl (±) N-[[[2-[[(phenylamino)-carbonyl]-thio]-1-benzyl)-ethyl]-amino]-carbonyl]-glycinate.

1.35 g of the product of Example 94, 15 ml of methylene chloride and 0.52 ml of phenyl isocyanate were mixed together at ambient temperature and stirred for 24 hours. 0.2 ml of phenyl isocyanate were added and the mixture was stirred for 12 hours. Another 0.2 ml of the reagent were added and stirring was carried out for a further 12 hours. The solvent was eliminated under reduced pressure and the residue was taken up in an ethyl acetate—methylene chloride mixture (2-8). After filtration and crystallization from ethyl acetate, 540 mg of the expected product melting at 152° C. to 154° C. were obtained.

EXAMPLE 96: (±) N-[[[2-[[(phenylamino)-carbonyl]-thio]-1-(phenylmethyl)-ethyl]-amino]-carbonyl]glycine.

1.11 g of the product of Example 12 in 15 ml of methylene chloride was cooled down to 0° C. and 1.2 ml of triethylamine and 0.49 ml of phenyl isocyanate dissolved in 5 ml of methylene chloride were added. The reaction medium was stirred for one hour, then poured into a solution of 10 ml of water and 8 ml of 2N hydrochloric acid. The precipitate was filtered, and dissolved in ethyl acetate. After elimination of the solvent under reduced pressure, 1.52 g of crude product were recovered, which was crystallized from ethyl acetate to obtain 0.983 g of the expected product melting at 179° C. to 181° C.

EXAMPLE 97: (±) S-[2-[[(4-methyl-1-piperazinyl)-carbonyl]-amino]-3-phenylpropyl]phenylthio carbamate and its hydrochloride.

Using the procedure of Example 96, 1.3 g of the hydrochloride of Example 34 and 0.64 ml of phenyl isocyanate were reacted and after purifying the base by chromatography on silica (eluant: methylene chloride—methanol 9-1), 1.15 g of the expected product melting at 120° C. were obtained.

Preparation of the hydrochloride 1 g of base was dissolved in 10 ml of ethyl acetate and a solution of hydrochloric acid in ethyl acetate was added until an acid pH was obtained. The mixture was refluxed and acetonitrile was added until dissolution was achieved, followed by ice-cooling, separating and drying under reduced pressure at 80° C. to obtain 0.78 g of the expected hydrochloride melting at 214° C.

EXAMPLE 98: (±) (3,4-dichlorophenyl) carbamothioate of S-[2-[[(4-methyl-1-piperazinyl)-carbonyl]-amino]-3-phenylpropyl]and its hydrochloride.

Using the procedure of Example 97, 1 g of the product of Example 34 in the form of the base and 0.56 g of 3,4-dichlorophenyl isocyanate were reacted to obtain isocyanate. 1.4 g of the expected product in the form of the base melting at 160° C. 1.2 g of the base were converted into the hydrochloride to obtain 0.8 g of the expected hydrochloride melting to 200° C.

EXAMPLE 99: (±) (4-methoxyphenyl) carbamothioate of S-[2-[[(4 -methyl-1-piperazinyl)-carbonyl]-amino]-3-phenylpropyl](E)-butene-dioate [1,2].

Using the procedure of Example 97, 1 g of the product of Example 34 in the form of the base and 0.42 ml of 4-methoxyphenyl isocyanate were reacted to obtain 1.1 g of product in the form of the base melting at 160° C.

Preparation of the fumarate 500 mg of base were dissolved in 30 ml of isopropanol and 0.14 g of fumaric acid in 10 ml of isopropanol were added. The mixture was ice-cooled, separated and dried under reduced pressure at 80° C. to obtain 0.6 g of the expected fumarate melting at 198° C.

EXAMPLE 100: (±) 2-[[(4-methyl-1-piperazinyl)-carbonyl]-amino]-3-phenylpropyl ethanethioate hydrochloride.

1.2 g of the product of Example 33 were dissolved in ethyl acetate and a solution of 2N hydrochloric acid in ethyl acetate was added. The solution was concentrated under reduced pressure and was taken up in acetone. The crystals were separated out and dried under reduced pressure to obtain 1.16 g of the expected hydrochloride melting at 184° C. to 186° C.

EXAMPLE 101: 2-[[(4-methyl-1-piperazinyl)-carbonyl]-amino-3-phenylpropyl (S)-ethanethioate and its hydrochloride.

Using the procedure of Example 1, 2.5 g of S-[2-isocyanato-3-phenylpropyl] (S)-ethanethioate and 1.44 ml of N-methyl piperazine were reacted to obtain 2.1 g of the expected product in the form of the base melting at 68° C. to 70° C.

Formation of the hydrochloride

Using the procedure of Example 100, 1.2 g of base were reacted to obtain 1.1 g of the expected hydrochloride melting at 188° C. to 190° C.

Preparation of the S-[2-isocyanato-3-phenyl-propyl](S)-ethanethioate

Using the procedure of Preparation 1, Steps A to F, (L)-phenylalanine was reacted.

EXAMPLE 102: (S) (−) N-[1-(mercaptomethyl)-2-phenylethyl]-4-methyl-1-piperazine carboxamide Using the procedure of Example 2, 1.675 g of the product of Example 101 in the form of the base and 0.266 ml of hydrazine hydrate were reacted to obtain 460 mg of the expected product melting at 68° C. to 70° C.

EXAMPLE 103: 2-[[(4-methyl-1-piperazinyl)-carbonyl]-amino]-3-phenylpropyl (R)-ethanethioate and its hydrochloride Using the procedure of Example 101, 2.45 g of isomer (R) were reacted to obtain 2.73 g of the expected product in the form of the base melting at 68° C. to 70° C. From 1.2 g of base, 1 g of the expected hydrochloride melting at 188° C. to 190° C. were obtained.

Preparation of S-(2-isocyanato-3-phenyl-propyl) (R)-ethanethioate for Example 103

STEP A: N-t-Boc-D-phenylalaninol 6.07 g of aluminium-lithium hydride in 200 ml of tetrahydrofuran was stirred while adding 21.2 g of N-t-Boc-D-phenylalanine in 250 ml of tetrahydrofuran at a temperature of less than 45° C. and the mixture was stirred for one hour. The mixture was cooled down to ambient temperature and 30 ml of a tetrahydrofuran—water mixture (1-1), then 50 ml of a saturated aqueous solution of sodium and potassium tartrate were added. After filtering and washing with tetrahydrofuran, the filtrate was concentrated under reduced pressure. The residue was taken up in water and extracted with methylene chloride. The solvent was eliminated and the residue was crystallized from hexane to obtain after drying, 12.2 g of the expected product melting at 94° C. to 96° C.

STEP B: 1,1-dimethylethyl (R) [1-[[[(4-methylphenyl)-sulfonyl]oxy]-methyl]-2-phenethyl] carbamate 11.3 g of the product of Step A were dissolved in 110 ml of methylene chloride and 8.25 g of 4-dimethylaminopyridine, then 10.68 g of tosyl chloride were added. The mixture was stirred for 2 hours at ambient temperature and the reaction medium was poured into 150 ml of an aqueous solution of 2N hydrochloric acid until a pH of 1 was obtained. The organic phase was separated out and dried and the solvents were eliminated under reduced pressure to obtain 18.2 g of the expected product melting at 110° C. to 112° C.

STEP C: (R) S-[2-[[(1,1-dimethylethoxy]-carbonyl]-amino]-3-phenylpropyl]ethanethioate 7.36 g of potassium thioacetate were added at ambient temperature to a solution of 17.415 g of the product of Step B in 170 ml of dimethylformamide and after stirring for 2 hours, the reaction medium was poured into water and extracted with ether. The solvent was eliminated under reduced pressure and the residue was chromatographed on silica (eluant: ethyl acetate—n-hexane 8-2) to obtain 9 g of the expected product melting at 92° C. to 94° C.

STEP D: S-(2-amino-3-phenylpropyl) (R) ethanethioate hydrochloride 85 ml of a solution of 4N hydrochloric acid in ethyl acetate were added to 8.5 g of the product of Step C in solution in 30 ml of ethyl acetate and after stirring for 2 hours, the solvents were eliminated. The residue was taken up in ether and the crystals formed were separated out and dried under reduced pressure to obtain 6.4 g of the expected product melting at 170° C. to 172° C.

STEP E: S-(2-isocyanato-3-phenylpropyl)-ethanethioate

Using the procedure of Step F of Preparation 1, 2.45 g of the product of Step D were reacted to obtain 2.5 g of the expected product which was used as is for Example 103.

EXAMPLE 104: (R) (+) N-[1-(mercaptomethyl)-2-phenyl ethyl]-4-methyl-1-piperazine carboxamide and its hydrochloride Using the procedure of Example 59, 2.35 g of the product of Example 103 in the form of the base were reacted to obtain after the addition of an aqueous solution of sodium bicarbonate, 1.520 g of the expected product in the form of the base melting at 68° C. to 70° C. Using the same procedure but without the addition of sodium bicarbonate, 1.848 g of the expected hyrochloride melting at 170° C. were obtained.

EXAMPLE 105: (+) S,S'-[2,2'-[carbonyl-bis-(imino)]-bis-(3-phenyl-propyl)]bis ethanethioate Using the procedure of Example 1, 2.35 g of the isocyanate of Step F of the preparation and 2.45 g of (±) S-(2-amino-3-phenyl-propyl)-ethanethioate hydrochloride of Step E of the preparation were reacted to obtain 1.4 g of the expected product melting at 144° C. to 146° C.

EXAMPLE 106: N,N'-bis-[1-(mercaptomethyl)-2-phenylethyl]urea

Using the procedure of Example 2, 1.776 g of the product of Example 105 and 0.426 ml of hydrazine hydrate were reacted to obtain 1.250 g of the expected product melting at 136° C. to 138° C.

EXAMPLE 107: S-[2-[[[(3-pyridinyl)-amino]-carbonyl]-amino]-3-phenylpropyl]ethanethioate Using the procedure of Example 1, 3 g of the isocyanate of Step F of the preparation and 1.2 g of 3-aminopyridine were reacted to obtain after purification on silica (eluant: methylene chloride), 2.5 g of the expected product.

EXAMPLE 108: (+) N-[1-(mercaptomethyl)-2-phenylethyl]-N'-(3-pyridinyl) urea

Using the procedure of Example 2, 1.5 g of the product of Example 107 and 0.24 ml of hydrazine hydrate were reacted to obtain 0.78 g of the expected product melting at 149° C.

EXAMPLE 109: (+) S-[2-[[1-(4-methylpiperazinyl)-carbonyl]-amino]-3-phenylpropyl]ethanethioate Using the procedure of Example 1, 3.7 g of the thiocyanate of Step F of the preparation and 2.4 ml of 1-amino-4-methylpiperazine were reacted to obtain about 5 g of product in the form of the base, which was converted into the hydrochloride by the addition of a solution of hydrochloric acid in ethyl acetate. The dihydrochloride was obtained and converted into the monohydrochloride by the addition of an aqueous solution of sodium bicarbonate. After crystallization from ethyl acetate, 1.5 g of the expected product melting at 158° C. to 160° C. were obtained.

EXAMPLE 110: [+] N-[1-(mercaptomethyl]-2-phenylethyl]-N'-(4-methyl -1-piperazinyl]-urea and its hydrochloride Using the procedure of Example 59, 2 g of the product of Example 109 were reacted to obtain 1 g of the expected product in the form of the base and then 0.56 g of hydrochloride melting at 198° C. to 200° C. were obtained.

EXAMPLE 111: (+) S-[2-[[hexahydro-1H-1-(4-methylazepinyl)-carbonyl]-amino]-3-phenylpropyl]ethanethioate Using the procedure of Example 1, 3 g of the isocyanate of Step F of the preparation and 1.6 g of N-methyl homopiperazine were reacted to obtain 2.6 g of the expected product.

EXAMPLE 112: (+) hexahydro-N-[(2-mercaptomethyl]-2-phenyl-ethyl]-4-methyl-1H-1,4-diazepin-1-carboxamide and its hydrochloride Using the procedure of Example 59, 2 g of the product of Example 111 were reacted to obtain 1.3 g of the expected product in the form of the base. 1.2 g of the base were converted into the hydrochloride to obtain 0.7 g of the expected hydrochloride melting at 162° C.

EXAMPLE 113: (+) N-[1-(mercaptomethyl)-2-phenylethyl]-4-methyl-1-piperazine acetamide dihydrochloride, trihydrate 2 g of (±) S-[2-[[(1,1-dimethylethoxy)-carbonyl]-amino]-3-phenylpropyl]-4-methyl-1-piperazine ethanethioate in 20 ml of methylene chloride in the presence of 4 ml of trifluoroacetic acid were stirred for 4 hours at ambient temperature and the solvents were then evaporated under reduced pressure to obtain 2.4 g of oily residue which was dissolved in water. The solution was alkalized with a saturated aqueous solution of sodium bicarbonate and extracted with ethyl acetate. The extracts were dried and the solvent was evaporated to obtain 1.1 g of product which was converted into its hydrochloride by the addition of an ethanolic solution of hydrochloric acid to obtain 0.6 g of the expected product melting at 170° C.

Preparation of the starting product of Example 113: (+) S-[2-[[(1,1-dimethylethoxy]-carbony]-amino]-3-phenylpropyl]-4-methyl-1-piperazine ethanethioate A mixture of 2.5 g of 2-(t-butoxy-carbonylamino) phenyl propanoic acid in 125 ml of methylene chloride with 1.77 g of 4-methyl-1-piperazine acetic acid (Journal of Pharmaceutical Sciences, Vol. 63 No. 12, (Dec. 1974), p. 1883) and 1.47 g of N-(3-dimethylaminopropyl)-N'-ethylcarbodiimide hydrochloride and 0.57 g of dimethylaminopyridine was stirred for 20 hours and the mixture was diluted with water and extracted with methylene chloride. The extracts were washed with water and dried and the solvent was evaporated off to obtain 3 g of crude product which yielded after chromatography on silica (eluant: methylene chloride—methanol 9-1), 2.25 g of the expected product melting at 104° C.

Preparation of the reagents

A) Preparation of allyl piperazine dihyrochloride of Example 64

STEP A: Ethylpiperazine N-allyl-N-carboxylate 15 g of ethyl piperazine N-carboxylate in 150 ml of ethanol were refluxed in the presence of 8.5 ml of allyl bromide and 13.1 g of potassium carbamate. The mixture was diluted with water and extracted with ethyl acetate. The solvent was evaporated off and the residue was chromatographed on silica (eluant: ethyl acetate—triethylamine 9-1) to obtain 15.5 g of the expected product.

STEP B: Allyl piperazine dihydrochloride 8 g of the product of Step A in 26 ml of water and 26 ml of hydrochloric acid was refluxed for 24 hours and the solvent was evaporated off. Crystallization took place from an ethyl acetate—isopropyl ether mixture to obtain 4.79 g of the expected product melting at 230° C.

B) Preparation of the 1-isopropyl piperazine dihydrochloride of Example 66

STEP A: Ethyl piperazine N-isopropyl-N-carboxylate 10 ml of ethyl piperazine N-carboxylate in 100 ml of ethanol were refluxed for 24 hours in the presence of 10.37 g of potassium carbonate and 7.05 ml of bromo-propane. The mixture was diluted with water and extracted with methylene chloride. The solvent was evaporated off and the residue was chromatographed on silica (eluant: ethyl acetate—triethylamine 9-1) to obtain 9 g of expected product.

STEP B: 1-isopropyl piperazine dihydrochloride

Using the procedure of Preparation A, 7 g of the product of Step A were reacted to obtain 5 g of the expected product melting at 250° C.

C) Preparation of 1-(2-propynyl)-piperazine used in Example 68

STEP A: Ethyl N-(2-propynyl)-piperazin-N-carboxylate

Using the procedure of Preparation B, Step A), 13.8 ml of ethyl piperazine N-carboxylate, 13.1 g of potassium carbonate and 8.4 ml of propargyl bromide were reacted to obtain 14 g of the expected product.

STEP B: 1-(2-propynyl) piperazine 2.67 g of the product of Step A) in 5 ml of ethanol, 0.66 ml of water and 4.4 g of potassium hydroxide were refluxed for 4 hours and extraction was carried out with ethyl acetate. The solvent was evaporated off and the residue was taken up in water. Extraction was carried out again with a tetrahydrofuran—ethyl acetate mixture (4-6) to obtain 0.2 g of the expected product.

EXAMPLE 114:

Tablets were prepared containing 100 mg of the Product of Example 1 and sufficient excipient for a tablet weighing 400 mg of lactose, talc, starch and magnesium stearate.

BIOLOGICAL STUDY

1) Determination of the enkephalinase inhibiting effect

The enkephalinase activity was determined from a renal membrane fraction of a rat. The kidneys were removed on ice and homogenized in a HEPES 0.05M pH 7.5 buffer containing magnesium chloride (50 times the volume). After a first centrifugation at 1,500 g, the specific fraction was obtained from a centrifugation at 15,000 g for 20 minutes. The deposit was then washed and suspended in a HEPES buffer and kept at −20° C. An aliquot of this membrane preparation was put in the presence of octyl beta-D-glucopyranoside (50 mM as final centrifugation) for 15 minutes at 4° C. After centrifugation at 100,000 g for one hour, the supernatant was removed and frozen in aliqots at −20° C. The concentration of proteins was determined by the method using Comassie's blue.

An aliquot of the protein fraction thus prepared was preincubated at 25° C. for 10 minutes in a HEPES 0.05M pH 7.5 buffer or in the presence of the product to be studied. The substrate added was a non-natural enkephalin of formula Succinyl-Ala-Ala-Phe-amino-methylcoumarine (reference 1) (40mM as final concentration). The incubation continued at 37° C. for 30 minutes and then the reaction was stopped by heating to 95° C. for 5 minutes and each incubate was centrifuged. A solution of amino peptidase M (4 mM as final concentration) and thiorphan (reference 2) ($10^{-5}$M) was added to the supernatant and the mixture was taken to 37° C. for one hour. The reaction was stopped as previously described and the fluorescence of 7-amino-methyl-coumarine produced was determined. The effect of the products to be tested was determined by calculating the $IC_{50}$, the concentration which inhibited the hydrolysis of the substrate by 50%.

Reference 1: R. A. Munford, P. A. Pierzchala, A-W Strauss and M. Zimmerman, Purification of a membrane-bound metalloendo peptidase from porcine kidney that degrades peptides hormones. Proc. Natl. Acad. Sci 78, No. 11, p. 6623.

Reference 2: Inhibitor of enkephalinase described in Example 20 of French Patent No. 2,480,747.

Results:

| Product of Example | $IC_{50}$ in $10^{-8}$ M |
| --- | --- |
| 6 | 0.35 |
| 17 | 4.8 |
| 16 | 7 |
| 1 | 8.7 |
| 15 | 10 |
| 18 | 18 |

2) Study of analgesic activity in a mouse Stretchings caused by acetic acid in a mouse The test used was based on the fact indicated by KOSTER, et al [Fed. Proc. (1959), Vol. 1B, p. 412] according to which the intraperitoneal injection of acetic acid causes, in a mouse, repeated stretching and twisting movements which can persist for more than 6 hours. Analgesics prevent or lessen this syndrome which can be considered as the outward display of a widespread abdominal pain. A 1% solution of acetic acid in water was used and was administered at a volume of 10 ml/kg. The studied product was administered by buccal route half-an-hour before the acetic acid injection, the mice having gone without food for at least 6 hours. The stretchings were observed and counted for Each mouse for an observation period of 15 minutes. The results were expressed by means of the $DA_{50}$, that is the dose which allows a decrease of 50% in the number of stretchings to be obtained relative to the control animals.

| Product | $DA_{50}$ in mg/kg PO |
| --- | --- |
| 18 | 33 |
| 16 | 50 |
| 1 | 71 |
| 11 | 85 |

3) Hot-plate test

Male mice weighing 22 g were placed individually on a copper plate maintained at 56° C. by a thermostatically-controlled water bath. The reaction to pain was displayed by licking one or both of the back paws. The reaction time to the heat stimulus was noted and only animals reacting within 4.5 and 6.5 seconds were retained. The reaction time to the pain was measured 30 minutes after oral administration. The variations in the reaction time were expressed as a percentage of the initial time. The $DA_{50}$ and $DA_{100}$, or doses which increased the reaction time by 50 and 100%, taking into account variations in the control group, were determined by a graph or by the method of the least squares.

| | in mg/kg/po | |
| --- | --- | --- |
| Product | $DA_{50}$ | $DA_{100}$ |
| Ex 18 | 33 | 100 |
| Ex 5 | 100 | 200 |
| Ex 11 | 100 | — |

The compounds are inhibitors of the neutral endopeptidase EC 3.4.24.11. This enzyme was implicated in particular in the degradation of enkephalines and the auricular natriuretic peptide (or ANF). The ANF is a powerful vasodilatory, diuretic and natriuretic peptide. The inhibition of the neutral endopeptidase EC 3.4.24.11 by the compounds described above can lead to a potentialization of the biological effects of the ANF. In particular, the hemodynamic, diuretic and natriuretic effects of these compounds are useful in the treatment of cardiac insufficiency, renal insufficiency, hypertension combined or not with a hyperreninhemia, hyperaldosteronism, oedemas of various origins, glacucoma. These compounds also have a therapeutic use in the treatment of gastro-intestinal disorders (of which in particular diarrehea and irritable colon) as well as congnitive disorders.

Various modifications of the compounds and method of the invention may be made without departing from the spirit or scope thereof and it is to be understood that the invention is intended to be limited only as defined in the appended claims.

What we claim is:

1. A compound selected from the group consisting of mercapto-alkylamines in all possible racemic, enantiomeric and diastereoisomeric forms of the formula

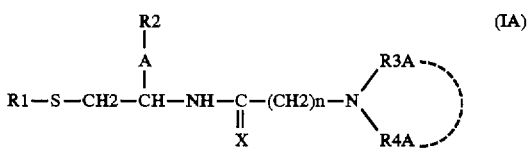

(IA)

wherein n is an integer from 0 to 4; $R_1$ is hydrogen or —CO—$R_5$, $R_5$ is selected from the group consisting of optionally substituted alkyl of 1 to 6 carbon atoms, optionally substituted alkenyl of 2 to 6 carbon atoms, optionally substituted alkynyl of 2 to 6 carbon atoms, optionally substituted and optionally unsaturated monocyclic rings of 5 to 7 ring members or of 8 to 10 ring members;

A is selected from the group consisting of a single bond, alkylene of 1 to 6 carbon atoms and alkenylene of 2 to 6 carbon atoms, the latter two optionally substituted with —OH or alkoxy of 1 to 6 carbon atoms; $R_2$ is optionally substituted monocyclic ring of 5 to 7 members or condensed rings of 8 to 10 ring members optionally interrupted with at least one heteroatom selected from the group consisting of —O—, —S— and nitrogen; X is oxygen or sulfur, $R_{3A}$ and $R_{4A}$ together with the nitrogen to which they are attached form an optionally substituted heterocycle selected from the group consisting of pyrrolidinyl, azepinyl, 1,4-diazepinyl, piperidyl, morpholinyl, and thiomorpholinyl;

and their non-toxic, pharmaceutically acceptable acid addition salts, the optional substituents on a) the alkyl, alkenyl, alkynyl and b) the monocyclic rings or condensed rings, aryl and aryloxy, being selected from the group consisting of halogen, hydroxyl, cyano, mercapto, nitro, acyl or up to 6 carbon atoms, acyloxy of up to 6 carbon atoms, free, salified or esterified carboxy, alkoxycarbonyl of up to 6 carbon atoms, alkyl, alkenyl, alkynyl, alkylthio, cycloalkyl, cycloalkenyl, heterocyclic hydrocarbons, aryl, aryloxy, arylthio, phenylalkyl and phenylalkoxy, all optionally substituted by 1 or 2 members selected from the group consisting of halogen, hydroxyl, trifluoromethyl, nitro, alkyl, alkenyl, aryl, alkoxy of up to 6 carbon atoms, acyl of up to 6 carbon atoms, free, salified or esterified carboxy, acylamido in which the acyl has up to 6 carbon atoms, carbamoyl and amino, said amino being optionally substituted on the nitrogen atom by 1 or 2 members of the group consisting of hydroxyl, alkyl of 1 to 6 carbon atoms and alkoxy to 1 to 6 carbon atoms.

2. A compound of claim 1 having the formula

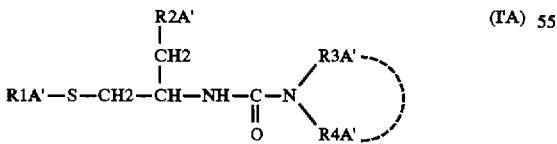

(I'A)

wherein $R'_1$ is hydrogen or $R'_{5A}$—CO—, $R'_{5A}$ is selected from the group consisting of phenyl, cycloalkyl, cycloalkenyl, alkyl of up to 6 carbon atoms and alkenyl of up to 6 carbon atoms, all optionally substituted;

$R_2'$ is selected from the group consisting of phenyl, naphthyl, benzyl phenethyl, indolyl, cycloalkyl and cycloalkenyl, all optionally substituted;

$R_{3A}'$ and $R'_{4A}$ together with the nitrogen atom to which they are attached form an optionally substituted heterocycle selected from the group consisting of pyrrolidinyl, azepinyl, 1,4-diazepinyl, piperidyl, morpholinyl and thiomorpholinyl;

all optionally substituted by 1 or 2 members of the group consisting of halogen, hydroxyl, trifluoromethyl, alkyl, alkenyl, alkynyl, alkoxy and phenyl, the last 5 groups being optionally substituted by 1 or 2 members of the group consisting of halogen, trifluoromethyl, hydroxyl, alkyl of 1 to 6 carbon atoms and alkoxy of 1 to 6 carbon atoms, the last two groups being optionally substituted by phenyl;

the optional substituents that can be carried by $R_1'$, $R_2'$ and $R_5'$ being selected from the group consisting of halogen, hydroxyl, cyano, nitro, acyl of up to 6 carbon atoms, acyloxy of up to 6 carbon atoms, benzoyl, free, salified or esterified carboxy, alkoxy of 1 to 6 carbon atoms; alkyl, alkenyl, cyclopentyl, cyclohexyl, cyclopentenyl, cyclohexenyl, phenyl, naphthyl, indolyl, phenoxy, benzyl, phenethyl, benzyloxy, all optionally substituted by at least 1 or 2 members of the group consisting of halogen, hydroxyl, trifluoromethyl, nitro, alkyl, alkenyl of up to 6 carbon atoms, alkoxy of up to 6 carbon atoms, formyl, acetyl, benzoyl, free, salified or esterified carboxy, acetamido, benzoylamido, carbamoyl, acylamido in which the acyl has up to 6 carbon atoms and amino, the latter being optionally substituted on the nitrogen atom by one or two members of the group consisting of hydroxyl, methyl, ethyl, propyl, methoxy, ethoxy and propoxy.

3. A compound of claim 1 of the formula

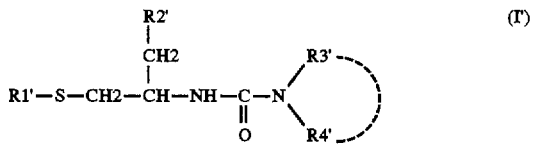

(I')

wherein $R_1$ is hydrogen or $R_5'$ —CO— where $R_5'$ is selected from the group consisting of phenyl, cycloalkyl, cycloalkenyl, alkyl of up to 6 carbon atoms and alkenyl of up to 6 carbon atoms, all optionally substituted;

$R_2'$ is selected from the group consisting of phenyl, naphthyl, benzyl, phenethyl, indolyl, cycloalkyl and cycloalkenyl, all optionally substituted;

$R_3'$ and $R_4'$ form with the nitrogen atom to which they are attached an optionally substituted heterocycle selected from the group consisting of pyrrolidinyl, azepinyl, 1,4-diazepinyl, piperidyl, morpholinyl and thiomorpholinyl, all optionally substituted by 1 or 2 members selected from the group consisting of halogen, hydroxyl, trifluoromethyl, alkyl, alkoxy and phenyl, the latter three groups being optionally substituted by 1 or 2 members of the group consisting of halogen, trifluoromethyl, hydroxyl, alkyl of 1 to 6 carbon atoms and alkoxy of 1 to 6 carbon atoms;

the optional substituents that can be carried by $R_1'$, $R_2'$ and $R_5'$ being selected from the group consisting of halogen, hydroxyl, cyano, nitro, acyl of up to 6 carbon atoms, acyloxy of up to 6 carbon atoms, benzoyl, free, salified or esterified carboxy of 1 to 6 carbon atoms; alkoxy of 1 to 6 carbon atoms; alkyl, alkenyl, cyclopentyl, cyclohexyl, cyclopentenyl, cyclohexenyl, phenyl, naphthyl, indolyl, phenoxy, benzyl, phenethyl and benzyloxy, and all optionally substituted by 1 or 2 members of the group consisting of halogen, hydroxyl, trifluoromethyl, nitro, alkyl of up to 6 carbon atoms, alkenyl of up to 6 carbon atoms, alkoxy of up to 6 carbon atoms, formyl, acetyl, benzoyl, free, salified or esterified carboxy, acetamido, benzoyiamido, carbamoyl and amino, the latter being optionally substituted on the nitrogen atom by one or two members of the group consisting of hydroxyl, methyl, ethyl, propyl, methoxy, ethoxy and propoxy.

4. A compound of claim 2 wherein $R_1'$ is hydrogen or acetyl, $R_2'$ is phenyl and $R_{3A}'$ and $R_{4A}'$ form with the nitrogen atom to which they are attached a member of the group consisting of piperidinyl, morpholinyl, dimethylmorpholinyl, thiomorpholinyl, pyrrolidinyl, azepinyl, 1,4 diazepinyl optionally substituted on the second nitrogen atom by alkyl of 1 or 2 carbon atoms.

5. An analgesic composition comprising an analgesically effective amount of at least one compound of claim 1 an inert carrier.

6. A method of relieving pain in warm-blooded animals comprising administering to warm-blooded animals an analgesically effective amount of a compound of claim 1.

7. A compound of claim 1 selected from the group consisting of S-[2[[(1-pyrrolidinyl)-carbonyl]-amino]-3-phenyl-propyl]ethanethioate;

(±)N-[2-mercapto-1-(phenylmethyl)-ethyl]-1-pyrrolidinecarboxamide;

(±)S-[2-[[hexahydro-1H-1-azepinyl)]-carbonyl]-amino]-3-phenylpropyl]ethanethioate;

(±)hexahydro-N-[2-mercapto-1-(phenylmethyl)ethyl]1H azepine-1carboxamide;

S-[2-[[(1-piperidinyl)carbonyl]amino]-3-phenylpropyl] ethanethioate;

(±)N-[2-mercapto-1-(phenylmethyl)-ethyl]-1-pyridine carboxamide;

S-[2-[[(4-thiomorpholinyl)-carbonyl]-amino]-3-phenyl ethyl]ethanethioate;

(±)N-[2-mercapto-1-(phenylmethyl)-ethyl]-4-thiomorpholine-carboxamide;

S-[2-[[(4-morpholinyl)-carbonyl]-amino]-3-phenyl propyl]ethanethioate;

(±)N-[2-mercapto-1-(phenylmethyl)-ethyl]-4-morpholine, carboxamide;

S-[2-[[[4-(cis-2,6-dimethyl)-morpholinyl]-carbonyl]-amino]-3-phenyl propyl]ethanethioate;

(±)cis-2,6-dimethyl-N-[2-mercapto-1-(phenylmethyl)-ethyl]-4-morpholine carboxamide;

S-[2-[[(hexahydro-1H-1,4-diazepin-1-yl)-carbonyl]-amino]-3-phenylpropyl]ethanethioate;

(±)hexahydro-N-[1-(mercaptomethyl)-2-phenylethyl]-1H-1,4-diazepin-1-carboxamide;

and their non-toxic, pharmaceutically acceptable acid addition salts.

8. An analgesic composition comprising an analgesically effective amount of at least one compound of claim 7 and an inert carrier.

9. A method of relieving pain in warm-blooded animals comprising administering to warm-blood animals an analgesically effective amount of at least one compound of claim 7.

* * * * *